(12) United States Patent
Chen et al.

(10) Patent No.: US 7,879,875 B2
(45) Date of Patent: Feb. 1, 2011

(54) P38 KINASE INHIBITING AGENTS

(75) Inventors: Meng-Hsin Chen, Westfield, NJ (US);
James B. Doherty, Montvale, NJ (US);
Robert Tynebor, Hatfield, PA (US);
Swaminathan R. Natarajan, Scotch Plains, NJ (US); Zhen Li, Scotch Plains, NJ (US); Soumya P. Sahoo, Old Bridge, NJ (US)

(73) Assignee: Merk Sharp & Dohme Corp., Rahway, NJ (US)

( * ) Notice: Subject to any disclaimer, the term of this patent is extended or adjusted under 35 U.S.C. 154(b) by 542 days.

(21) Appl. No.: 11/990,050

(22) PCT Filed: Aug. 8, 2006

(86) PCT No.: PCT/US2006/030962
§ 371 (c)(1),
(2), (4) Date: Feb. 1, 2008

(87) PCT Pub. No.: WO2007/021710
PCT Pub. Date: Feb. 22, 2007

(65) Prior Publication Data
US 2009/0131472 A1 May 21, 2009

Related U.S. Application Data

(60) Provisional application No. 60/708,034, filed on Aug. 12, 2005.

(51) Int. Cl.
*A61K 31/4375* (2006.01)
*C07D 455/02* (2006.01)

(52) U.S. Cl. .................................... 514/306; 546/138
(58) Field of Classification Search ................ 514/306; 546/138
See application file for complete search history.

(56) References Cited

FOREIGN PATENT DOCUMENTS

WO    WO 98 27098    6/1998

*Primary Examiner*—Sreeni Padmanabhan
*Assistant Examiner*—Sahar Javanmard
(74) *Attorney, Agent, or Firm*—Maria V. Marucci; Valerie J. Camara

(57) ABSTRACT

Compounds described by the chemical formula (I) or pharmaceutically acceptable salts thereof: (I) are inhibitors of p38 and are useful in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

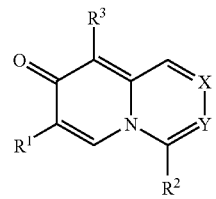

(I)

7 Claims, No Drawings

P38 KINASE INHIBITING AGENTS

CROSS REFERENCE TO RELATED APPLICATIONS

This application is a U.S. National Phase application under 35 U.S.C. §371 of PCT Application No. PCT/US2006/030962, filed Aug. 8, 2006, which claims priority under 35 U.S.C. §119(e) from U.S. Provisional Application Ser. No. 60/708,034, filed Aug. 12, 2005.

BACKGROUND OF THE INVENTION

The present invention relates to heterobicyclic compounds that inhibit the action of the p38 mitogen-activated protein kinase, a mammalian protein kinase that is involved in cell proliferation, cell response to stimuli, and cell death. In particular, this invention relates to heterobicyclic compounds that are selective and potent inhibitors of the p38 mitogen-activated protein kinase. This invention also relates to pharmaceutical compositions containing such heterobicyclic compounds that inhibit the p38 mitogen-activated protein kinase.

Related Background

Mitogen-activated protein ("MAP") kinases mediate the surface-to-nucleus signal transduction in a cell. Protein kinases that activate and phosphorylate MAP are known as mitogen-activated protein kinase kinases ("MKK"). One such MKK specifically phosphorylates and activates the p38 MAP kinase ("p38") and is called MKK3. U.S. Pat. Nos. 5,736,381 and 5,804,427 describe human mitogen-activated kinase kinase isoforms. International Publication No. 98/00539 describes a human gene encoding an MKK3-Interacting Protein.

Xia et al., *Science*, 270, 1326-1331 (1995) describes the p38 signal transduction pathway as being activated by proinflammatory cytokines and environmental stress. MKK3 is described as being involved in transducing stress signals such as nerve growth factor mediated apaptosis in PC12 cells. It is believed that inhibition of p38 activity can provide relief from acute and chronic inflammation by blocking production of cytokines such as IL-1 and TNF, thereby inhibiting the production of proinflammatory cytokines such as IL-6 and IL-8. In particular, it is believed that p38 inhibitors block the synthesis of TNFα and IL-1β cytokines, thereby providing relief from inflammatory diseases such as arthritis. Accordingly, it would be desirable to provide novel compounds that are selective and potent inhibitors of the action of p38.

International Publication No. 97122704 describes the mitogen-activated protein kinase kinase MEK6, which can stimulate phosphorylation and activation of p38 substrates. International Publication Nos. 95/31451, 99/00357 and 98/27098 describe various inhibitors of p38. Nonetheless, there remains a great need to develop inhibitors of the action of p38 for various pharmaceutical and therapeutic applications.

SUMMARY OF THE INVENTION

Compounds described by the chemical formula (I) or pharmaceutically acceptable salts thereof:

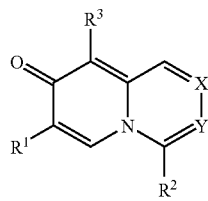

(I)

are inhibitors of p38.

DETAILED DESCRIPTION OF THE INVENTION

The present invention provides P38 inhibitor compounds of the chemical formula (I):

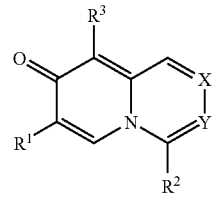

(I)

or a pharmaceutically acceptable salt thereof, wherein:
X and Y are each independently selected from —$CR^4$— and —N—;
$R^1$ is selected from:
  (1) hydrogen,
  (2) halogen,
  (3) OH, and
  (4) alkoxy;
$R^2$ is selected from:
  (1) $NR^a$,
  (2) aryl,
  (3) heteroaryl,
  (4) heterocycloalkyl, and
  (5) $OR^a$;

said heteroaryl, aryl and heterocycloalkyl are each optionally substituted with one or more substituents selected from $R^6$, $R^7$ and $R^8$;
$R^3$ is selected from:
  (1) aryl,
  (2) benzyl,
  (3) heteroaryl, and
  (4) heterocycloalkyl;

said heteroaryl, aryl and heterocycloalkyl are each optionally substituted with one or more substituents selected from $R^6$, $R^7$ and $R^8$;
$R^4$ is selected from:
  (1) hydrogen,
  (2) $C_1$-$C_6$ alkyl,
  (3) alkoxy,
  (4) CHO,
  (5) $CONH_2$,
  (6) $C(O)_2R^a$,
  (7) $C_0$-$C_4$alkyl-OH,
  (8) O—$C_1$-$C_4$ alkyl,
  (9) halogen,
  (10) aryl,
  (11) heteroaryl,
  (12) heterocycloalkyl,
  (13) $COR^a$,
  (14) O—$C_1$-$C_4$alkyl-N—C(O)—$C_0$-$C_2$alkyl($R^bR^c$)—$NH_2$,
  (15) heterocycloalkyl-C(O)—$C_0$-$C_2$alkyl($R^bR^c$)—$NH_2$,
  (16) N($R^a$)($R^a$),
  (17) O—$R^a$,
  (18) N—C(O)—N-heterocycloalkyl,
  (19) O—C(O)—N-heterocycloalkyl,
  (20) N—$C_1$-$C_4$alkyl-N—$R^a$, and
  (21) N—$C_1$-$C_4$alkyl-O—$R^a$;

said heteroaryl and aryl are each optionally substituted with one or more substituents selected from $R^6$, $R^7$ and $R^8$;
$R^6$, $R^7$ and $R^8$ are each independently selected from:
  (1) halogen,
  (2) $C_1$-$C_6$ alkyl,
  (3) CN, (4) OR$^a$,
(5) alkoxy,
(6) cycloalkyl,
(7) C=R$^a$(R$^a$),
(8) CON(R$^a$)(R$^a$),
(9) aryl,
(10) N(R$^a$)(R$^a$),
(11) heteroaryl,
(12) hydrogen,
(13) C$_1$-C$_4$—OH,
(14) heterocycloalkyl,
(15) CON-alkyl-CO$_2$—R$^a$,
(16) CON-alkyl-CON(R$^a$)(R$^a$),
(17) CON-alkyl-N(R$^a$)(R$^a$),
(18) C(=O)R$^a$, and
(19) C(O)$_2$R$^a$;

said heteroaryl and aryl are each optionally substituted with one or more substituents selected from R$^a$;
R$^a$ is selected from:
(1) hydrogen,
(2) halogen,
(3) NH—C$_1$-C$_4$ alkyl,
(4) C$_1$-C$_6$ alkyl,
(5) C$_1$-C$_4$-alkyl-heteroaryl,
(6) C$_1$-C$_4$-alkyl-cycloalkyl,
(7) heteroaryl,
(8) C$_1$-C$_4$alkyl-heterocycloalkyl,
(9) heterocycloalkyl,
(10) C$_0$-C$_4$alkyl-NH$_2$, and
(11) C$_0$-C$_4$alkyl-OH;

R$^b$ and R$^c$ are each independently selected from hydrogen and alkyl, or R$^b$ and R$^c$ can join together to form a cycloalkyl.

Additional embodiments of the present invention include compounds of the Formula Ia:

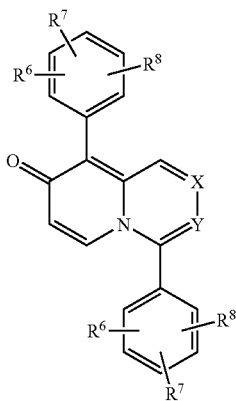

(Ia)

or a pharmaceutically acceptable salt thereof, wherein:
X and Y are each independently selected from —CR$^4$— and —N—;
R$^4$ is selected from:
(1) hydrogen,
(2) C$_1$-C$_6$ alkyl,
(3) alkoxy,
(4) CHO,
(5) CONH$_2$,
(6) C(O)$_2$R$^a$,
(7) C$_0$-C$_4$alkyl-OH,
(8) O—C$_1$-C$_4$ alkyl,
(9) halogen,
(10) aryl,
(11) heteroaryl,
(12) heterocycloalkyl,
(13) COR$^a$,
(14) O—C$_1$-C$_4$alkyl-N—C(O)—C$_0$-C$_2$alkyl(R$^b$R$^c$)—NH$_2$,
(15) heterocycloalkyl-C(O)—C$_0$-C$_2$alkyl(R$^b$R$^c$)—NH$_2$,
(16) N(R$^a$)(R$^a$),
(17) O—R$^a$,
(18) N—C(O)—N-heterocycloalkyl,
(19) O—C(O)—N-heterocycloalkyl,
(20) N—C$_1$-C$_4$alkyl-N—R$^a$, and
(21) N—C$_1$-C$_4$alkyl-O—R$^a$;

said heteroaryl and aryl are each optionally substituted with one or more substituents selected from R$^6$, R$^7$ and R$^8$;
R$^6$, R$^7$ and R$^8$ are each independently selected from:
(1) halogen,
(2) C$_1$-C$_6$ alkyl,
(3) CN,
(4) OR$^a$,
(5) alkoxy.
(6) cycloalkyl,
(7) C=R$^a$(R$^a$),
(8) CON(R$^a$)(R$^a$),
(9) aryl,
(10) N(R$^a$)(R$^a$),
(11) heteroaryl,
(12) hydrogen,
(13) C$_1$-C$_4$—OH,
(14) heterocycloalkyl,
(15) CON-alkyl-CO$_2$—R$^a$,
(16) CON-alkyl-CON(R$^a$)(R$^a$),
(17) CON-alkyl-N(R$^a$)(R$^a$),
(18) C(=O)R$^a$, and
(19) C(O)$_2$R$^a$;

said heteroaryl and aryl are each optionally substituted with one or more substituents selected from R$^a$; and
R$^a$ is selected from:
(1) hydrogen,
(2) halogen,
(3) NH—C$_1$-C$_4$ alkyl,
(4) C$_1$-C$_6$ alkyl,
(5) C$_1$-C$_4$-alkyl-heteroaryl,
(6) C$_1$-C$_4$-alkyl-cycloalkyl,
(7) heteroaryl,
(8) C$_1$-C$_4$alkyl-heterocycloalkyl,
(9) heterocycloalkyl,
(10) C$_0$-C$_4$alkyl-NH$_2$, and
(11) C$_0$-C$_4$alkyl-OH;

R$^b$ and R$^c$ are each independently selected from hydrogen and alkyl, or R$^b$ and R$^c$ can join together to form a cycloalkyl.

Further embodiments of the present invention include compounds of the Formula Ib:

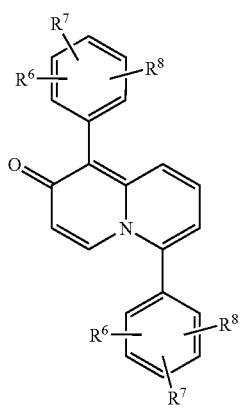

(Ib)

or a pharmaceutically acceptable salt thereof, wherein:
$R^6$, $R^7$ and $R^8$ are each independently selected from:
(1) halogen,
(2) $C_1$-$C_6$ alkyl,
(3) CN,
(4) $OR^a$,
(5) $CON(R^a)(R^a)$,
(6) aryl,
(7) heteroaryl,
(8) $C=R^a(R^a)$,
(9) hydrogen,
(10) $C_1$-$C_4$—OH,
(11) $C(=O)R^a$, and
(12) $C(O)_2R^a$;

said heteroaryl and aryl are each optionally substituted with one or more substituents selected from $R^a$; and
$R^a$ is selected from:
(1) hydrogen,
(2) halogen,
(3) NH—$C_1$-$C_4$ alkyl,
(4) $C_1$-$C_6$ alkyl,
(5) $C_1$-$C_4$-alkyl-heteroaryl,
(6) $C_1$-$C_4$-alkyl-cycloalkyl,
(7) heteroaryl,
(8) $C_1$-$C_4$alkyl-heterocycloalkyl,
(9) heterocycloalkyl,
(10) $C_0$-$C_4$alkyl-$NH_2$, and
(11) $C_0$-$C_4$alkyl-OH.

Still further embodiments of the present invention include compounds of the Formula Ic:

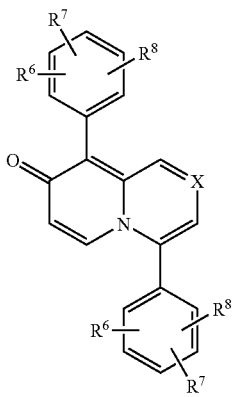

(Ic)

a pharmaceutically acceptable salt thereof, wherein:
—$CR^4$—;
$R^4$ is selected from:
(1) hydrogen,
(2) $C_1$-$C_6$ alkyl,
(3) alkoxy,
(4) $CONH_2$,
(5) $C(O)_2R^a$,
(6) $C_0$-$C_4$alkyl-OH,
(7) O—$C_1$-$C_4$ alkyl,
(8) aryl,
(9) heteroaryl,
(10) heterocycloalkyl,
(11) $COR^a$,
(12) O—$C_1$-$C_4$alkyl-N—C(O)—$C_0$-$C_2$alkyl($R^bR^c$)—$NH_2$,
(13) heterocycloalkyl-C(O)—$C_0$-$C_2$alkyl($R^bR^c$)—$NH_2$,
(14) $N(R^a)(R^a)$,
(15) O—$R^a$,
(16) N—C(O)—N-heterocycloalkyl,
(17) O—C(O)—N-heterocycloalkyl,
(18) N—$C_1$-$C_4$alkyl-N—$R^a$, and
(19) N—$C_1$-$C_4$alkyl-O—$R^a$;

said aryl and heteroaryl are each optionally substituted with one or more substituents selected from $R^6$, $R^7$ and $R^8$;
$R^6$, $R^7$ and $R^8$ are each independently selected from:
(1) halogen,
(2) $C_1$-$C_6$ alkyl,
(3) CN,
(4) $OR^a$,
(5) aryl,
(6) $C=R^a(R^a)$,
(7) heteroaryl,
(8) hydrogen,
(9) $C_1$-$C_4$—OH, and
(10) $C(=O)R^a$;

said heteroaryl and aryl are each optionally substituted with one or more substituents selected from $R^a$;
$R^a$ is selected from:
(1) hydrogen,
(2) halogen,
(3) NH—$C_1$-$C_4$ alkyl,
(4) $C_1$-$C_6$ alkyl,
(5) $C_1$-$C_4$-alkyl-heteroaryl,
(6) $C_1$-$C_4$-alkyl-cycloalkyl,
(7) heteroaryl,
(8) $C_1$-$C_4$alkyl-heterocycloalkyl,
(9) heterocycloalkyl,
(10) $C_0$-$C_4$alkyl-$NH_2$, and
(11) $C_0$-$C_4$alkyl-OH;

$R^b$ and $R^c$ are each independently selected from hydrogen and alkyl, or $R^b$ and $R^c$ can join together to form a cycloalkyl.

Additional embodiments of the present invention include compounds of the Formula Id:

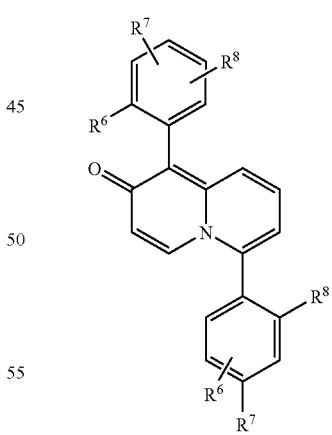

(Id)

or a pharmaceutically acceptable salt thereof, wherein:
$R^6$, $R^7$ and $R^8$ are each independently selected from:
(1) halogen,
(2) $C_1$-$C_6$ alkyl,
(3) CN,
(4) $OR^a$,
(5) $CON(R^a)(R^a)$,
(6) aryl, (7) heteroaryl,
(8) hydrogen,
(9) $C_1$-$C_4$—OH,
(10) C(=O)$R^a$, and
(11) C(O)$_2R^a$;

said heteroaryl and aryl are each optionally substituted with one or more substituents selected from $R^a$;

$R^a$ is selected from:
(1) hydrogen,
(2) halogen,
(3) NH—$C_1$-$C_4$ alkyl,
(4) $C_1$-$C_6$ alkyl,
(5) $C_1$-$C_4$-alkyl-heteroaryl,
(6) $C_1$-$C_4$-alkyl-cycloalkyl,
(7) heteroaryl,
(8) $C_1$-$C_4$alkyl-heterocycloalkyl,
(9) heterocycloalkyl,
(10) $C_0$-$C_4$alkyl-$NH_2$, and
(11) $C_0$-$C_4$alkyl-OH.

As used herein, "alkyl" means carbon chains that have no double or triple bonds, and that may be linear or branched or combinations thereof. Thus, $C_1$-$C_6$ alkyl is defined to identify the group as having 1, 2, 3, 4, 5 or 6 carbons in an arrangement that is linear, branched, or a combination thereof. Examples of alkyl groups include methyl, ethyl, propyl, n-propyl, isopropyl, butyl, sec- and tert-butyl, pentyl, hexyl, heptyl and the like. The term "$C_0$-$C_4$alkyl" includes alkyls containing 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_2$-$C_6$ alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_2$-$C_6$ alkynyl is defined to identify the group as having 2, 3, 4, 5 or 6 carbon in a linear or branched arrangement, such that $C_2$-$C_6$ alkynyl specifically includes 2-hexynyl and 2-pentynyl.

The term "alkoxy" as used herein, alone or in combination, includes an alkyl group connected to the oxy connecting atom, and alkyl ether groups, wherein the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "aryl," unless specifically stated otherwise, is intended to mean any stable monocyclic or fused bicyclic carbon ring of up to 7 members in each ring, wherein at least one ring is aromatic. Examples of such aryl elements include phenyl, napthyl and tolyl.

The term "aryloxy" unless specifically stated otherwise includes multiple ring systems as well as single ring systems such as, for example, phenyl or naphthyl, connected through the oxy connecting atom to the connecting site.

The term "hetero," unless specifically stated otherwise, includes one or more O, S, or N atoms. For example, heterocycloalkyl and heteroaryl include ring systems that contain one or more O, S, or N atoms in the ring, including mixtures of such atoms. The hetero atoms replace ring carbon atoms.

Examples of heterocycloalkyls include azetidinyl, pyrrolidinyl, piperidinyl, piperazinyl, morpholinyl, tetrahydrofuranyl, imidazolinyl, pyrrolidin-2-one, piperidin-2-one and thiomorpholinyl. As used herein, "heterocycloalkyl" includes bridged heterocycloalkyls having two or more heterocycloalkyl groups joined via adjacent or non-adjacent atoms.

The term "heteroaryl", as used herein except where noted, is intended to mean a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, pyridine, pyrimidine, pyrazine, thiophene, oxazole, thiazole, triazole, thiadiazole, oxadiazole, pyrrole, 1,2,4-oxadiazole, 1,3,4-oxadiazole, 1,2,4-thiadiazole, 1,3,4-thiadiazole, and 1,2,4-triazole.

Additional examples of heteroaryl include quinolinyl, pyrimidinyl, isoquinolinyl, pyridazinyl, quinoxalinyl, furyl, benzofuryl, dibenzofuryl, thienyl, benzothienyl, indolyl, indazolyl, isoxazolyl, isothiazolyl, imidazolyl, benzimidazolyl, thiadiazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "amine" unless specifically stated otherwise includes primary, secondary and tertiary amines.

Unless otherwise stated, the term "carbamoyl" is used to include —NHC(O)O$C_1$-$C_4$alkyl, and —OC(O)NH$C_1$-$C_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$)alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Unless specifically stated otherwise or indicated by a bond symbol (dash or double dash), the connecting point to a recited group will be on the right-most stated group. That is, for example, a phenylalkyl group is connected to the main structure through the alkyl and the phenyl is a substituent on the alkyl.

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be mixtures of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from nontoxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomers. All such isomers, including optical isomers, being included in the present invention.

The invention described herein also includes a pharmaceutical composition which is comprised of a compound described by Formula (I), or a pharmaceutically acceptable salt thereof, in combination with a pharmaceutically acceptable carrier.

The invention described herein also includes a pharmaceutical composition which is comprised of a compound described by Formula (I), or a pharmaceutically acceptable salt thereof, in combination with a pharmaceutically acceptable carrier. The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists.

The invention described herein also includes a method of treating arthritis which is comprised of administering to a mammalian patient in need of such treatment a compound described by Formula (I), or a pharmaceutically acceptable salt thereof, in an amount which is effective to treat arthritis.

The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention includes methods of treating arthritis by administering to a mammalian patient in need of such treatment a compound described by Formula (I), or a pharmaceutically acceptable salt thereof, in combination or in coadministration with a COX-2 inhibitor.

The invention described herein also includes a method of treating a cytokine mediated disease in a mammal, comprising administering to a mammalian patient in need of such treatment an amount of a compound described by Formula (I), or a pharmaceutically acceptable salt thereof, in an amount which is effective to treat said cytokine mediated disease.

Of particular interest is a method of treating inflammation in a mammalian patient in need of such treatment, which is comprised of administering to said patient an anti-inflammatory effective amount of a compound described by Formula (I), or a pharmaceutically acceptable salt thereof.

Another method which is of particular interest is a method of treating a cytokine mediated disease as described herein wherein the disease is osteoporosis.

Another method which is of particular interest is a method of treating a cytokine mediated disease as described herein wherein the disease is non-osteoporotic bone resorption.

Yet another method which is of particular interest is a method of treating a cytokine mediated disease as described herein wherein the disease is Crohn's disease.

This invention also relates to a method of treating arthritis in a mammal in need such treatment, which comprises administering to said mammal an amount of a compound of formula I which is effective for treating arthritis. Such method includes the treatment of rheumatoid and osteoarthritis.

When administered to a patient for the treatment of athritis, the dosage used can be varied depending upon the type of arthritis, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

This invention also relates to a method of inhibiting the action of p38 in a mammal in need thereof, which comprises administering to said mammal an effective amount of a compound described by Formula (I), or a pharmaceutically acceptable salt thereof, to inhibit said action of p38, down to normal levels, or in some cases to subnormal levels, so as to ameliorate, prevent or treat the disease state.

The compounds of formula I can be used in the prophylactic or therapeutic treatment of disease states in mammals which are exacerbated or caused by excessive or unregulated cytokines, more specifically IL-1, IL-6, IL-8 or TNF.

Because the compounds of formula I inhibit cytokines, such as IL-1, IL-6, IL-8 and TNF, by inhibiting the action of p38 the compounds are useful for treating diseases in which cytokine presence or activity is implicated, such as pain, rheumatoid arthritis, rheumatoid spondylitis, osteoarthritis, gouty arthritis and other arthritic conditions.

The compounds described by Formula (I), or a pharmaceutically acceptable salt thereof, are also useful to treat other disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds described by Formula (I), or a pharmaceutically acceptable salt thereof, are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds described by Formula (I), or a pharmaceutically acceptable salt thereof, are also useful in treating diseases such as chronic obstructive pulmonary disease and diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound described by Formula (I), or a pharmaceutically acceptable salt thereof, in an amount which is effective for treating said disease or condition.

The compounds described by Formula (I), or a pharmaceutically acceptable salt thereof, are also useful for treating Alzheimer's disease. The instant invention thus includes a method of treating Alzheimer's disease in a mammal in need of such treatment, which comprises administering to said mammal a compound of Formula (I), or a pharmaceutically acceptable salt thereof, in an amount effective for treating said disease or condition.

When administered to a patient for the treatment of a disease in which a cytokine or cytokines are implicated, the dosage used can be varied depending upon the type of disease, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally advantageous. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, or, advantageously, one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

Assays

Protein Expression and Purification.

Murine p38 containing the FLAG epitope tag was expressed in *Drosophila* S2 cells under transcriptional control of a copper-inducible metallothionein promoter. Expression of recombinant p38 was induced by treating transfected cells with 1 mM $CuSO_4$ for 4 hours. To generate active recombinant murine p38, $CuSO_4$-treated S2 cells were stimulated 10 minutes prior to harvest with 400 mM NaCl, 2 mM $Na_3VO_4$, and 100 g/L okadaic acid. Cell pellets were washed with phosphate-buffered saline, 2 mM $Na_3VO_4$, and lysed in 20 mM Tris HCl, pH 7.5, 120 mM NaCl, 1% Triton X-100, 2 mM EDTA, 20 mM NaF, 4 mM $Na_3VO_4$, 2 mM Prefabloc SC (Boehringer Mannheim). Cell lysates were centrifuged for 10 min at 13,000×g, and activated, recombinant murine p38 was immunoaffinity purified from the lysate by column chromatography through anti-FLAG M2 resin (Kodak) that had been equilibrated with lysis buffer. After loading the extract the resin was washed with 10 column volumes of lysis buffer, 10 column volumes buffer A (10 mM Tris HCl, pH 7.5, 500 mM NaCl, 20% glycerol) and 10 column volumes of buffer B (10 mM Tris HCl pH 7.5, 150 mM NaCl, 20% glycerol). The fusion protein was eluted in buffer B containing 100 µg/mL FLAG peptide (Kodak).

The N-terminal 115 amino acids of ATF-2 was expressed in *E. coli* as a fusion protein with glutathione-S-transferase. The fusion protein was purified over glutathione agarose according to standard procedures (Pharmacia).

p38 Kinase Assay.

p38 kinase assays were performed in a reaction volume of 100 µL in a 96-well plate, at 30° for 45-1200 min under the following conditions: 25 mM Hepes, pH 7.4, 10 mMmgCl$_2$, 20 mM β-glycerolphosphate, 2 mM DTT, 5 µM ATP, 10 µCi[γ-$^{33}$P]-ATP and 2 µM GST-ATF2. Serial dilutions of compounds were added to each reaction in 2 µL DMSO. 2 µL of DMSO was added to the last row of each reaction plate as the no inhibitor control for each inhibitor titration. The reaction was terminated with an equal volume of a stop solution containing 100 mM EDTA and 15 mM sodium pyrophosphate. PVDF filter plates (MAIPNOB50, Millipore) were pre-wet with methanol and washed with the stop solution. 50 µL aliquots from a single reaction were applied to the filter under vacuum, and the filter was washed twice with 75 mM phosphoric acid. The filter plates were counted in a scintillation counter (Top Count, Packard) and the percent inhibition at each compound concentration is determined.

TNF-α Release Assay.

Blood was obtained from healthy volunteers by venipuncture using sodium heparin as an anti-coagulant. Peripheral blood mononuclear cells (PBMCs) were isolated using Lymphocyte Separation Medium (ICN) according to manufacturers specifications. Isolated PBMCs were washed 3 times with HBSS and diluted to a density of $2 \times 10^6$ cells/mL in RPMI+ 5% autologous human serum. 50 µL of the serial dilutions of inhibitor were added to wells of a 96-well tissue culture plate followed by addition of 100 µL of PBMCs and then 50 µL of RPMI complete medium containing 400 ng/mL LPS. A control well of cells without compound but with LPS (maximal stimulation control) and one without compound and without LPS (background control) were included in each titration. The cells were incubated for 16 hours in a humidified incubator at 37° C., 5% $CO_2$. Supernatants were then harvested and TNF-α levels were quantified by immunoassay using commercial reagents (R&D, Inc).

The compounds of this invention demonstrated efficacy in the above assays by results of less than 10 µM. Advantageous compounds had results less than 1 µM. Even more advantageous compounds had results less than 0.1 µM. Still more advantageous compounds had results in the assays of less than 0.01 µM.

The abbreviations used herein are as follows unless specified otherwise:
Bu butyl
Bn benzyl
BOC t-butyloxycarbonyl
BOP benzotriazol-1-yloxy tris/dimethylamino-phosphonium hexafluorophosphate
DCC dicyclohexylcarbodiimide
DME 1,2-dimethoxyethane
DMF N,N-dimethylformamide
DMAP 4-dimethylaminopyridine
EDC 1-(3-dimethylaminopropyl_3-ethylcarbodi-imide hydrochloride
EtOAc ethyl acetate
Eq. equivalent(s)
HOBt, HOBT hydroxybenztriazole
HPLC high pressure liquid chromatography
LAH lithium aluminum hydride
LCMS liquid chromatography-mass spectrophotometer
LHMDS lithium bis(trimethylsilyl)amide
MeOH methanol
MHz megahertz
MS (ES) mass spectrophotometer-electon spray
NMP N-methylpyrrolidinone
Ph phenyl
Pr propyl
TBAF tetrabutylammonium fluoride
TEA triethylamine
THF tetrahydrofuran
TMEDA N,N,N',N'-tetramethylethylenediamine
TLC thin layer chromatography
Tetrakis tetrakis(triphenylphosphine)palladium The present compounds can be prepared according to the general Schemes provided below as well as the procedures provided in the Examples. The following Schemes and Examples further describe, but do not limit, the scope of the invention. The substituents are the same as in the above Formulas except where defined otherwise or otherwise apparent to the ordinary skilled artisan.

The procedures described herein for synthesizing the compounds may include one or more steps of protecting group manipulations and of purification, such as, recrystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (LC-MS). Methods of protecting group manipulation, purification, structure identification and quantification are well known to one skilled in the art of chemical synthesis.

It is understood that the functional groups present in compounds described in the Schemes below can be further manipulated, when appropriate, using the standard functional group transformation techniques available to those skilled in the art, to provide desired compounds described in this invention.

Other variations or modifications, which will be obvious to those skilled in the art, are within the scope and teachings of this invention. This invention is not to be limited except as set forth in the following claims.

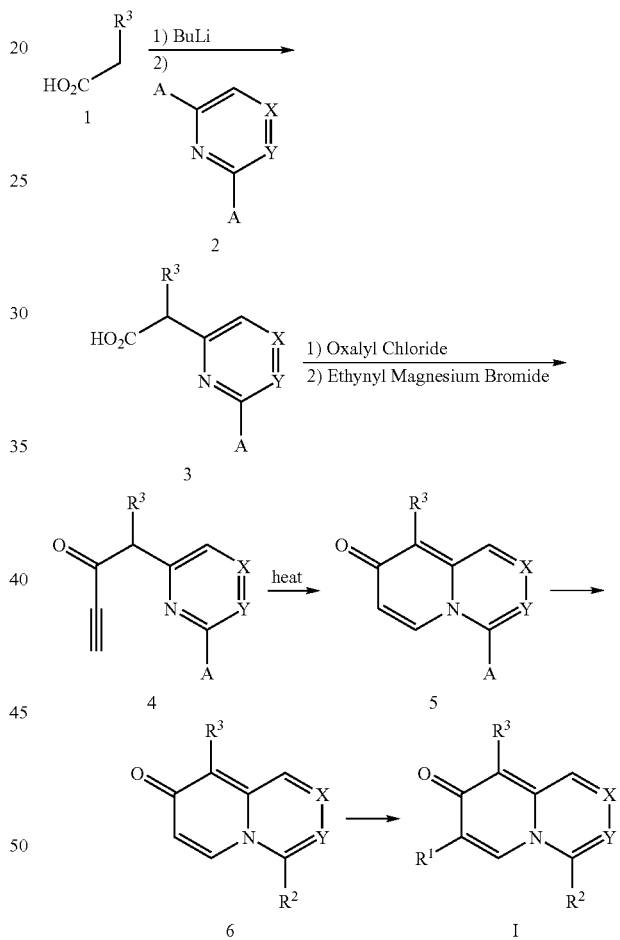

A = F, Cl, Br

Compounds of Formula I can be synthesized as described in Scheme 1. The appropriate dianion is generated by adding 2 eq. of butyl lithium to an aryl acetic acid 1 at low temperature in a proper solvent, such as THF. The resulting dianaion is reacted with compound 2 to yield compound 3 which is subsequently converted to the cyclization precursor 4. Cyclization of compound 4 can be achieved by heating in an inert solvent such as pyridine, TMEDA, toluene, DMF or NMP, to give compound 5, which can be used for the synthesis of compound 6 by a variety of reaction conditions, including standard Pd-mediated coupling reactions such as Suzuki;

Stille and Buchwald. Compounds of Formula I can be arrived at using methods known in the art.

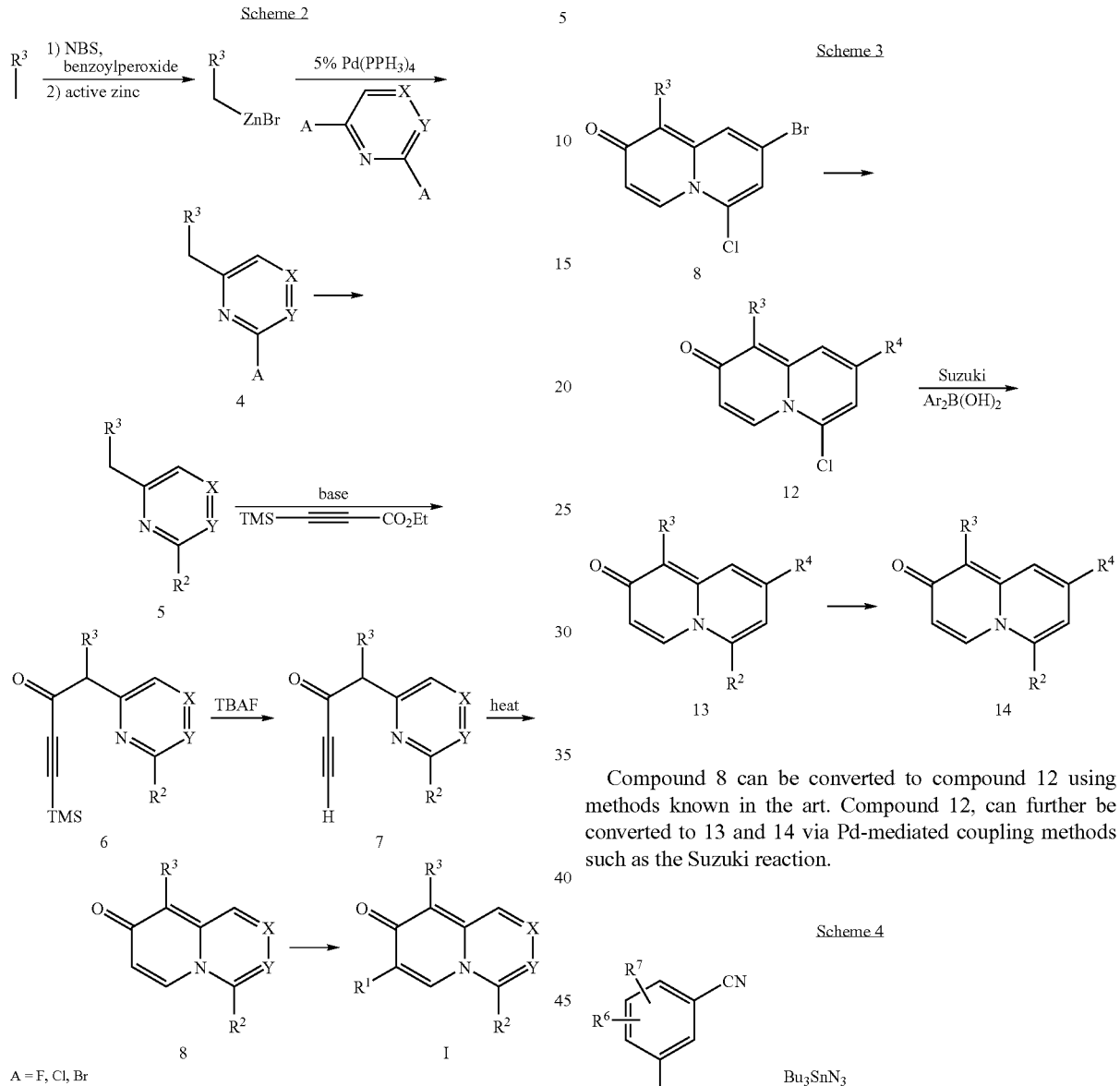

A = F, Cl, Br

Alternatively, compounds of Formula I can be synthesized as described in Scheme 2. Compound 4 can be prepared by literature procedures (Minato, A., Tamao, K., Hayashi, T., Suzuki, K., Kumada, M., *Tetrahedron Lett.*, (1980), 21, 845; and Andres, J. I., Alonso, J. M., Fernandez, J., Iturrino, L., Martinez, P., Meert, T. F., Sipido, V. K., *Bioorg Med Chem Lett.* (2002), 12 (24), 3573-3577). Compound 5 can be readily prepared from the compound 4 by any of several known procedures such as standard Pd-mediated coupling reactions or substitution reactions. Deprotonation of compound 5 which can be achieved by using a base such as lithium diisopropyl amide and lithium bis(trimethylsilyl)amide, in THF at low temperature and quenching the anion with propynoate to yield compound 6. Removal of the TMS protecting group can be carried out according to procedures known in the art to give compound 7, from which compound 8 can be prepared by using procedures similar to that described in Scheme 1. Compounds of Formula I can be prepared from compound 8 using methods known in the art.

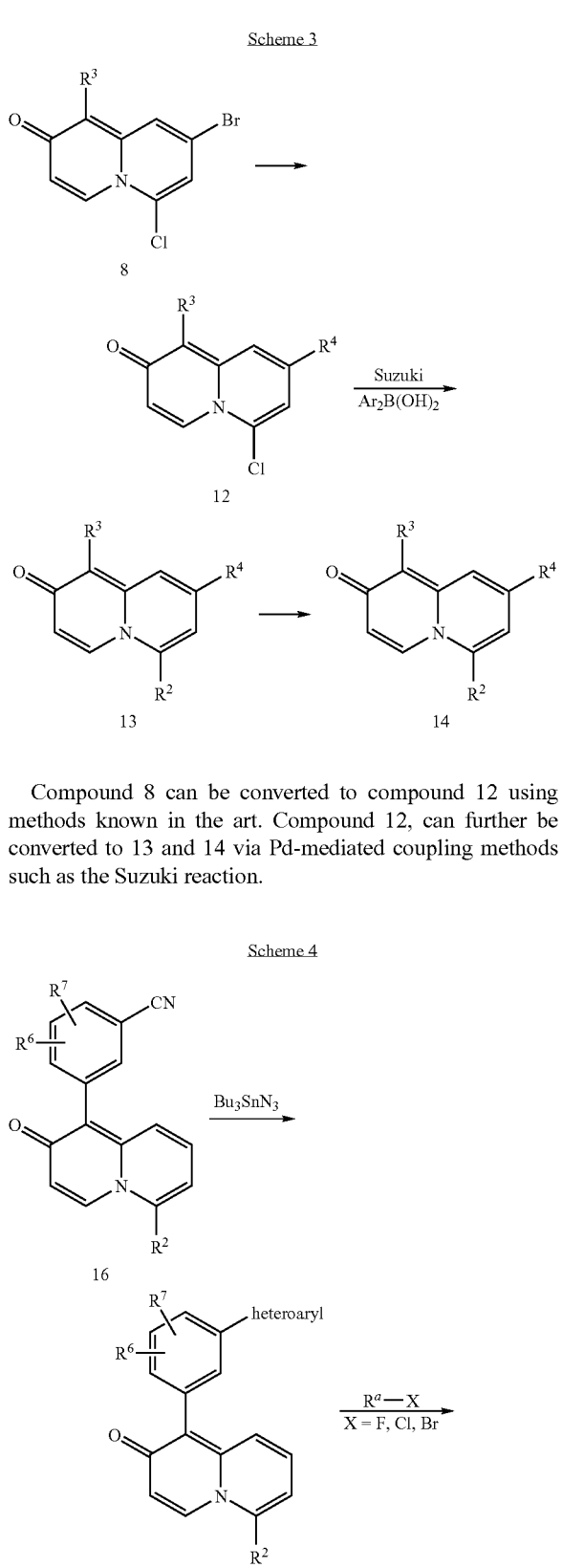

Compound 8 can be converted to compound 12 using methods known in the art. Compound 12, can further be converted to 13 and 14 via Pd-mediated coupling methods such as the Suzuki reaction.

-continued

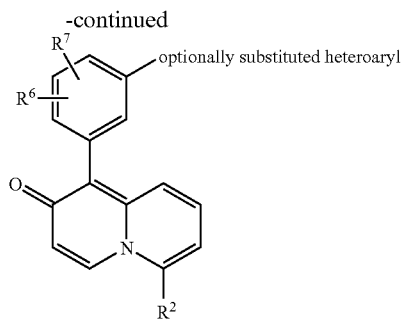

Scheme 6

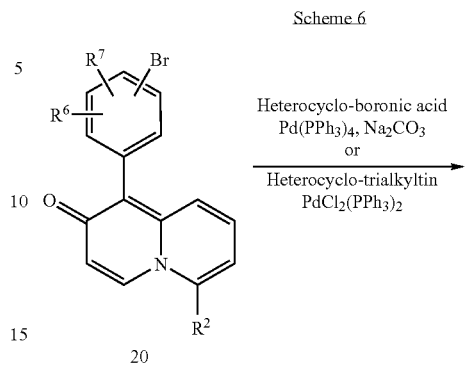

In Scheme 4, compound 16, which can serve as an intermediate, can be synthesized from commercial available starting material by using procedures similar to that described above. The nitrile functional group can be converted to a hetrocycle moiety by methods known in the art. For example, treating compound 16 with tributyl tin azide yields tetrazole derivatives.

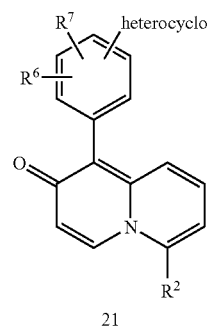

In Scheme 6, compound 21 can be achieved from intermediate 20 by employing a variety of reaction conditions, such as standard Pd-mediated coupling using commercially available heterocyclotin or heterocyclo-boronic acids.

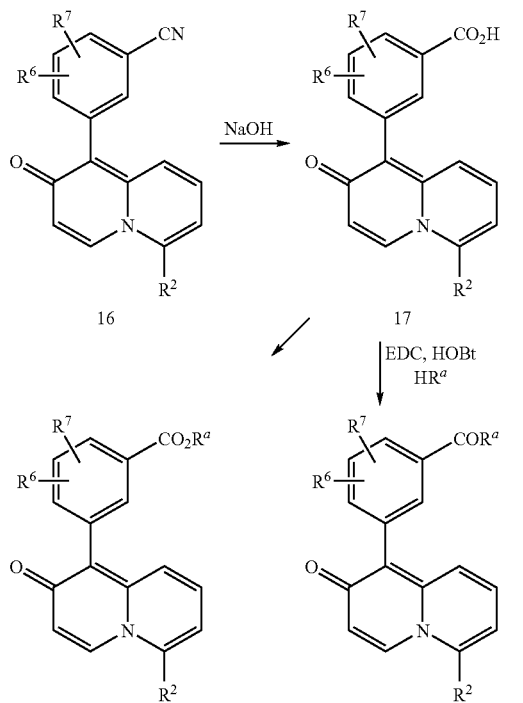

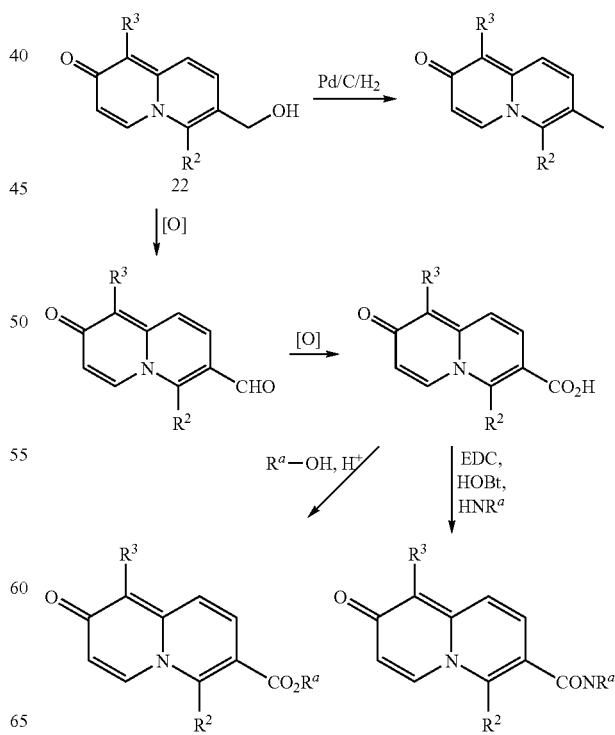

As shown in Scheme 5, hydrolysis of the nitrile 16 can be achieved by methods known to those skilled in the art to give the corresponding carboxylic acid 17. Under standard peptide coupling reaction conditions, the acid 17 can be converted to the amide. Standard peptide coupling reaction conditions mean coupling a carboxylic acid with an amine using an acid activating agent such as EDC, DCC or BOP in a proper solvent such as methylene chloride or DMF in the presence of HOBt. If an ester functional group is desired, 4-dimethylaminopyridine is used instead of HOBt, while employing standard peptide coupling reaction conditions. Alternatively, ester formation can also be accomplished between acid the 17 and an appropriate alcohol in presence of an acid.

Compound 22, which can be synthesized from 2,6-dichloronicotinc acid by the procedures described above, can serve as an intermediate to produce the instant compounds using methods commonly known in the art.

In some cases the final product may be further modified by, for example, manipulation of substituents. These manipulations may include, but are not limited to, reduction, oxidation, alkylation, acylation, halogenation and hydrolysis reactions which are commonly known to those skilled in the art. Unless specifically stated otherwise, starting materials and compounds are commercially available or otherwise known in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

EXAMPLE 1

Preparation of Intermediate 6-chloro-1-(2,6-dichlorophenyl)-2H-quinolizin-2-one

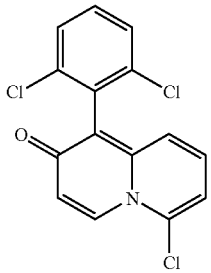

Step-A 1-(6-chloropyridin-2-yl)-1-(2,6-dichlorophenyl)but-3-yn-2-one

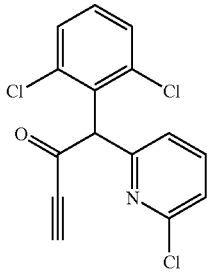

To a solution of 2,6-dichlorophenylacetic acid (4.1 g) in THF (100 mL) was added n-butyl lithium (1.4 M, in hexanes, 30 mL) slowly at 0° C. The resulting mixture was stirred at 0° C. for ½ hr and then cooled to −78° C. To this solution was added 2,6-dichloropyridine (2.96 g) at −78° C. then warmed to room temperature and stirred for approximately 1-3 hours. The mixture was re-cooled to −78° C. and oxalyl chloride (1.9 mL) was added. The resulting mixture was warmed to room temperature and stirred for 1 hr. The solution was re-cooled to −78° C. and ethynylmagnesium bromide (0.5 N, 44 mL) was added. The mixture was slowly warmed to room temperature. The reaction was quenched with 0.1 N HCl, and extracted with ether. The organic layer was separated, washed with brine solution, dried over magnesium sulfate, filtered, and evaporated. The residue was purified by silica gel (hexanes/methylene chloride=3/1) to give desired compound as a yellowish solid (0.59 g).

$^1$H NMR (CDCl$_3$, 500 MHz): δ 7.57 (t, 1H), 7.45 (d, 2H), 7.32 (t, 1H), 7.17 (d, 1H), 6.43 (d, 1H), 3.07 (s, 1H). MS (ES): 324.1 (M+H).

Step-B 6-chloro-1-(2,6-dichlorophenyl)-2H-quinolizin-2-one

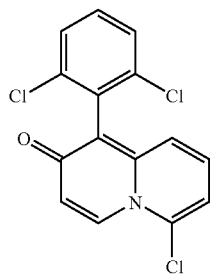

A solution of 1-(6-chloropyridin-2-yl)-1-(2,6-dichlorophenyl)but-3-yn-2-one (Step A above, 102 mg) in pyridine (7 mL) was heated to 90° C. for about 1½ hr and cooled to room temperature. The mixture was evaporated and purified by silica gel (methylene chloride/acetone=3/1) to give desired product as a yellowish solid (90 mg).

$^1$H NMR (CDCl$_3$, 500 MHz): δ 8.71 (d, 1H), 7.47 (d, 2H), 7.33 (t, 1H), 7.18 (d, 1H), 7.03 (dd, 1H), 6.86 (d, 1H), 6.72 (d, 1H). MS (ES): 323.9 (M+H).

EXAMPLE 2

6-(2-chlorophenyl)-1-(2,6-dichlorophenyl)-2H-quinolizin-2-one

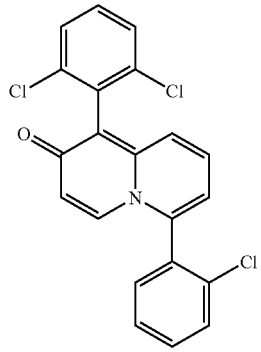

To a solution of 6-chloro-1-(2,6-dichlorophenyl)-2H-quinolizin-2-one (Example 1, 54 mg) in DME was added 2-chlorophenylboronic acid (31 mg), palladium acetate (3.5 mg), triphenylphosphine (8 mg) and 2N sodium carbonate (0.32 mL). The mixture was heated to 80° C. for 12 hrs, then cooled to room temperature, and diluted with ethyl acetate/ saturated aqueous sodium bicarbonate. The organic layers were dried over magnesium sulfate and concentrated. The residue was purified by silica gel (methylene chloride/acetone=2/1) and recrystallized from methylene chloride/acetone/hexanes to give title compound as a yellowish solid (28 mg).

$^1$H NMR (CDCl$_3$, 500 MHz): δ 7.70 (d, 1H), 7.64 (d, 1H), 7.61 (td, 1H), 7.57-7.49 (m, 4H), 7.34 (t, 1H), 7.23 (dd, 1H), 7.14 (m, 1H), 6.87 (d, 1H), 6.66 (d, 1H). MS (ES): 400.2 (M+H).

Examples 3-7 were made using procedures similar to that described in Example 2 above.

EXAMPLE 3

1-(2,6-dichlorophenyl)-6-(2-methylphenyl)-2H-quinolizin-2-one

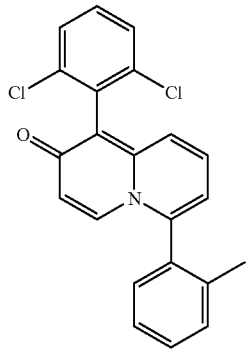

$^1$H NMR (CDCl$_3$, 500 MHz): δ 7.70 (d, 1H), 7.51 (td, 1H), 7.48 (d, 2H), 7.43-7.30 (m, 4H), 7.20 (dd, 1H), 6.90 (d, 1H), 6.80 (d, 1H), 6.60 (d, 1H), 2.13 (s, 3H). MS (ES): 380.3 (M+H).

EXAMPLE 4

2-[-(2,6-dichlorophenyl)-2-oxo-2H-quinolizin-6-yl]benzaldehyde

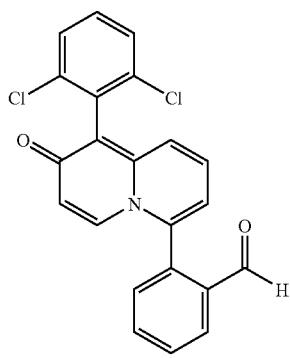

$^1$H NMR (CDCl$_3$, 500 MHz): δ 9.94 (s, 1H), 8.14 (d, 1H), 7.87 (m, 2H), 7.57 (m, 2H), 7.47 (m, 2H), 7.31 (t, 1H), 7.15 (dd, 1H), 6.80 (t, 2H), 6.53 (dd, 1H). MS (ES): 394.3 (M+H).

EXAMPLE 5

1-(2,6-dichlorophenyl)-6-(4-fluoro-2-methylphenyl)-2H-quinolizin-2-one trifluoroacetate

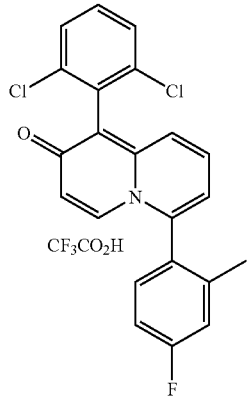

$^1$H NMR (CD$_3$OD, 500 MHz): δ 8.48 (d, 1H), 7.93 (t, 1H), 7.66 (d, 2H), 7.60-7.40 (m, 5H), 7.32 (dd, 1H), 7.27 (t, 1H), 2.11 (s, 3H). MS (ES): 398.1 (M+H).

EXAMPLE 6

1-(2,6-dichlorophenyl)-6-(2,4-difluorophenyl)-2H-quinolizin-2-one trifluoroacetate

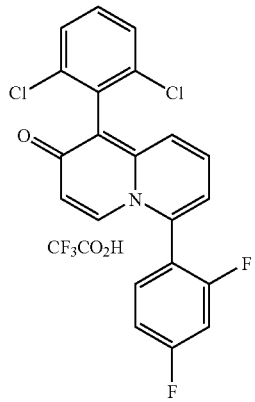

$^1$H NMR (CD$_3$OD, 500 MHz): δ 8.83 (d, 1H), 8.02 (t, 1H), 7.80 (m, 1H), 7.70-7.51 (m, 6H), 7.36 (m, 2H). MS (ES): 402.1 (M+H).

EXAMPLE 7

1-(2,6-dichlorophenyl)-6-(2-fluorophenyl)-2H-quinolizin-2-one

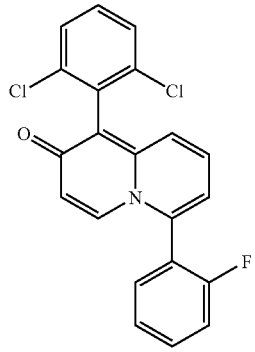

$^1$H NMR (CDCl$_3$, 500 MHz): δ 7.88 (d, 1H), 7.65 (m, 1H), 7.53-7.32 (m, 6H), 7.20 (dd, 1H), 7.05 (m, 1H), 6.85 (d, 1H), 6.69 (d, 1H). MS (ES): 384.1 (M+H).

EXAMPLE 8

1-(2,6-dichlorophenyl)-6-[2-(hydroxymethyl)phenyl]-2H-quinolizin-2-one

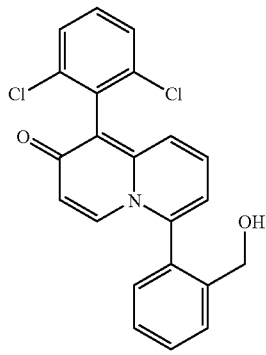

To a solution of 2-[1-(2,6-dichlorophenyl)-2-oxo-2H-quinolizin-6-yl]benzaldehyde (Example 4, 8 mg) in methanol was added sodium borohydride (2 mg) at 0° C. and stirred for ½ hr. The mixture was concentrated and purified by silica gel (methylene chloride/acetone=1/2) to give the title compound (4 mg).

$^1$HMR (CDCl$_3$, 500 MHZ): δ 7.81 (d, 1H), 7.73 (d, 1H), 7.57 (t, 2H), 7.48-7.28 (m, 5H), 7.22 (dd, 1H), 6.80 (d, 1H), 6.67 (d, 1H), 6.65 (d, 1H), 4.43 (abq, 2H). MS (ES): 396.1 (M+H).

EXAMPLE 9

1-(2,6-dichlorophenyl)-6-pyrrolidin-1-yl-2H-quinolizin-2-one

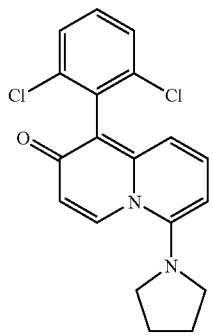

A mixture of 6-chloro-1-(2,6-dichlorophenyl)-2H-quinolizin-2-one (Example 1, 15 mg) in pyrrolidine (0.5 mL) was heated to 90° C. for 2½ hr and then concentrated. The residue was purified by silica gel (methylene chloride/acetone=3/1) to give title compound as a yellow solid (12 mg).

$^1$H NMR (CDCl$_3$, 500 MHz): δ 8.49 (d, 1H), 7.47 (d, 2H), 7.28 (t, 1H), 7.06 (m, 2H), 6.43 (d, 1H), 6.30 (d, 1H), 3.26 (m, 4H), 2.10 (m, 4H). MS (ES): 359.4 (M+H).

EXAMPLE 10

6-(cyclopropylmethoxy)-1-(2,6-dichlorophenyl)-2H-quinolizin-2-one

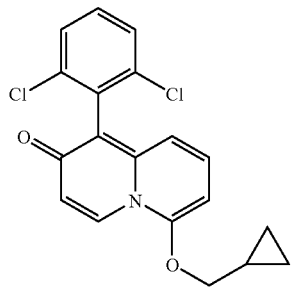

To oil free sodium hydride (24 mg) suspended in DMF was added cyclopropylmethanol (0.08 mL) at room temperature and stirred for ½ hr. To this mixture was added 6-chloro-1-(2,6-dichlorophenyl)-2H-quinolizin-2-one (Example 1, 15 mg) and stirred for approximately 1-3 hours. The mixture was diluted with ethyl acetate/water. The organic layers were washed with water (3×), brine, and dried over magnesium sulfate. Upon evaporation, the residue was purified by silica gel (methylene chloride/acetone=3/1) to give title compound (15 mg).

$^1$H NMR (CDCl$_3$, 500 MHz): δ 8.65 (d, 1H), 7.45 (d, 2H), 7.29 (t, 1H), 7.06 (dd, 1H), 7.00 (d, 1H), 6.32 (d, 1H), 5.90 (d, 1H), 4.10 (d, 2H), 1.43 (m, 1H), 0.81 (m, 2H), 0.48 (m, 2H). MS (ES): 360.1 (M+H).

EXAMPLE 11

6-(2,4-difluorophenyl)-1-(2,6-difluorophenyl)-2H-quinolizin-2-one

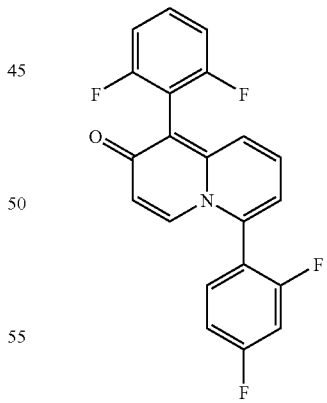

The title compound was prepared by the procedure described in Examples 1 and 2 using 2,6-difluorophenylacetic acid instead of 2,6-dichlorophenylacetic acid in Example 1, Step A and 2,4-difluorophenylboronic acid instead of 2-chlorophenylboronic acid in Example 2.

$^1$H NMR (CD$_3$OD, 500 MHz): δ 8.17 (dd, 1H), 7.67 (m, 1H), 7.46 (m, 1H), 7.44 (m, 1H), 7.28 (m, 2H), 7.14 (m, 3H), 6.96 (dd, 1H), 6.88 (d, 1H). MS (ES): 370.1 (M+H).

EXAMPLE 12

4-(2-chlorophenyl)-9-(2,6-dichlorophenyl)-8H-pyrido[1,2-a]pyrazin-8-one

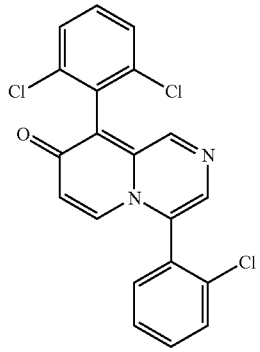

The title compound was prepared by the procedure described in Examples 1 and 2 using 2,6-dichloropyrazine instead of 2,6-dichloropyridine in Example 1, Step A.

$^1$H NMR (CDCl$_3$, 500 MHz): δ 8.36 (s, 1H), 7.70-7.52 (m, 8H), 7.40 (t, 1H), 7.14 (br d, 1H). MS (ES): 401.0 (M+H).

EXAMPLE 13

3-bromo-6-(2,4-difluorophenyl)-1-(2,6-difluorophenyl)-2H-quinolizin-2-one

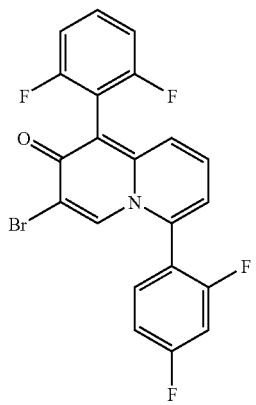

To a solution of 6-(2,4-difluorophenyl)-1-(2,6-difluorophenyl)-2H-quinolizin-2-one (Example 11, 78 mg, 0.211 mmol) in CH$_2$Cl$_2$ was added a solution of Br$_2$:CH$_2$Cl$_2$ (1:1) at room temperature. The reaction was stirred for a couple hours until complete by LCMS. The reaction mixture was concentrated in vacuo and the crude material was purified via silica gel chromatography (100% EtOAc).

$^1$H NMR (CDCl$_3$) δ: 8.18 (s, 1H), 7.48 (m, 1H), 7.42 (m, 1H), 7.12-7.22 (m, 3H), 7.05 (m, 3H), 6.60 (d, 1H).

EXAMPLE 14

6-(2-chlorophenyl)-1-(2,6-dichlorophenyl)-8-methoxy-2H-quinolizin-2-one

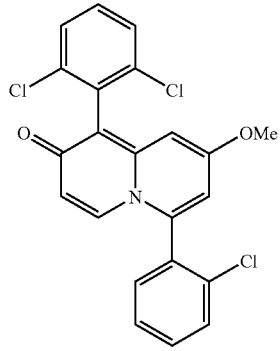

Step-A 2,6-dichloro-4-methoxypyridine

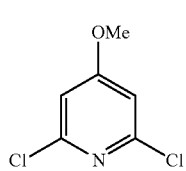

To a solution of 2,4,6-trichloropyridine (4.5 g) in methanol was added sodium methoxide (25% in methanol, 6.8 mL) at room temperature. The mixture was stirred for 12 h then poured into ethyl acetate/water and separated. The organic layer was washed with water, brine and dried over magnesium sulfate. Upon evaporating, the residue was purified by crystallization (100% hexanes) to give title compound as solid (3.1 g).

MS (ES): 178.3 (M+H).

Step-B 6-(2-chlorophenyl)-1-(2,6-dichlorophenyl)-8-methoxy-2H-quinolizin-2-one

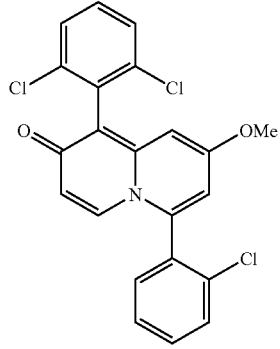

The title compound was prepared by the procedure described in Examples 1 and 2 using 2,6-dichloro-4-methoxypyridine instead of 2,6-dichloropyridine in Example 1, Step A.

$^1$H NMR (CDCl$_3$, 500 MHz): δ 7.63-7.49 (m, 6H), 7.46 (d, 1H), 7.31 (t, 1H), 6.70 (d, 1H), 6.31 (d, 1H), 5.86 (d, 1H), 3.70 (s, 3H). MS (ES): 430.3 (M+H).

EXAMPLE 15

6-(2-chlorophenyl)-1-(2,6-dichlorophenyl)-8-hydroxy-2H-quinolizin-2-one

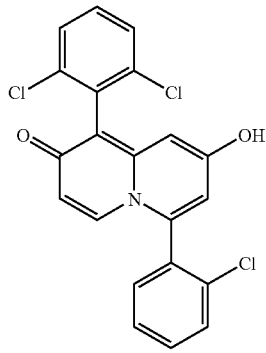

To a solution of 6-(2-chlorophenyl)-1-(2,6-dichlorophenyl)-8-methoxy-2H-quinolizin-2-one (Example 14, 40 mg) in methylene chloride was added boron tribromide (0.06 mL) at −78° C. The mixture was warmed to room temperature and stirred for 12 h. After quenching with 2N HCl, the mixture was extracted with methylene chloride, washed with brine, dried over magnesium sulfate and concentrated. The residue was purified by silica gel (methylene chloride/methano-=7/1) to give title compound (25 mg).

MS (ES): 416.1 (M+H).

EXAMPLE 16

6,8-bis(2-chlorophenyl)-1-(2,6-dichlorophenyl)-2H-quinolizin-2-one

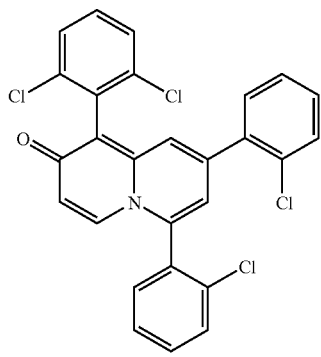

The title compound was prepared by the procedure described in Examples 1 and 2 using 2,4,6-trichloropyridine instead of 2,6-dichloropyridine in Example 1, Step A and 2 eq. of 2-chlorophenylboronic acid instead of 1 eq. of 2-chlorophenylboronic acid in Example 2.

MS (ES): 512.1 (M+H).

EXAMPLE 17

Preparation of Intermediate 8-bromo-6-chloro-1-(2,6-dichlorophenyl)-2,4-quinolizin-2-one

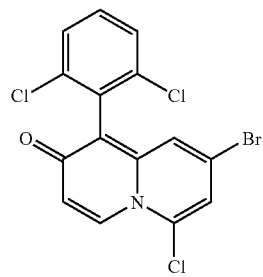

Step-A 4-bromo-2,6-dichloropyridine

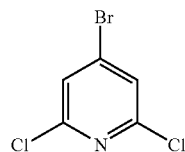

To a suspension of copper (II) bromide (8.2 g) in acetonitrile was added t-butylnitrile (5.5 mL) at 0° C. 4-amino-2,6-dichloropyridine (5.0 g) in acetonitrile. The mixture slowly warmed to room temperature and stirred for an additional 12 h. The mixture was poured into 2N HCl and extracted with ethyl acetate, washed with brine, dried over magnesium sulfate, and concentrated. The title compound was recrystallized from toluene/hexanes (4.5 g).

Step-B 8-bromo-6-chloro-1-(2,6-dichlorophenyl)-2H-quinolizin-2-one

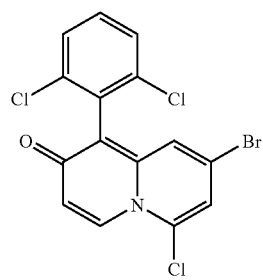

The title compound was prepared by the procedure described in Example 1 using 4-bromo-2,6-dichloropyrazine instead of 2,6-dichloropyridine in Step A.

$^1$H NMR (CD$_3$OD, 500 MHz): δ 9.01 (d, 1H), 7.58 (d, 2H), 7.48 (t, 1H), 7.40 (s, 1H) 7.04 (d, 1H), 6.89 (s, 1H).

EXAMPLE 18

Preparation of Intermediate 8-(1-tert-butyl-1,2,3,6-tetrahydropyridin-4-yl)-6-chloro-1-(2,6-dichlorophenyl)-2H-quinolizin-2-one

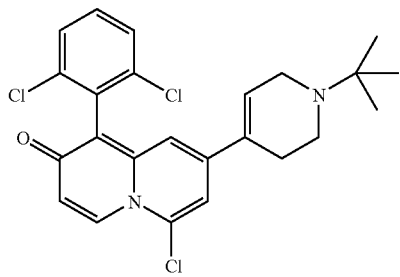

To a solution of 8-bromo-6-chloro-1-(2,6-dichlorophenyl)-2H-quinolizin-2-one (Example 17, 132 mg) in THF was added 1-t-butyl-4-(trimethylstannyl)-1,2,3,6-tetrahydropyridine (process route disclosed in U.S. Pat. No. 6,809,199, 90 mg.), dichlorobis(triphenylphosphine) palladium (21 mg) and heated to reflux for 12 h. The mixture was concentrated and purified by silica gel (methylene chloride/acetone=1/2) to give title compound (57 mg).
$^1$H NMR (CD$_3$OD, 500 MHz): δ 9.02 (d, 1H), 7.58 (d, 2H), 7.52 (s, 1H), 7.48 (t, 1H), 7.01 (d, 1H), 6.59 (s, 2H), 3.54 (br. s, 2H), 2.93 (br. s, 2H), 2.33 (br. s, 2H), 1.20 (s, 9H).

EXAMPLE 19

8-(1-tert-butyl-1,2,3,6-tetrahydropyridin-4-yl)-6-(2-chlorophenyl)-1-(2,6-dichlorophenyl)-2H-quinolizin-2-one hydrochloride

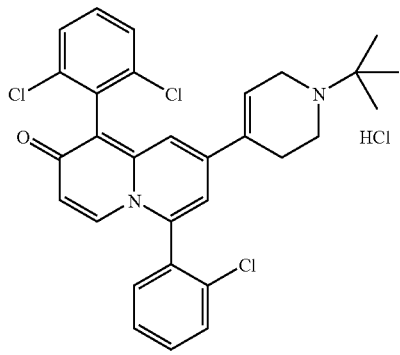

To a solution of 8-(1-tert-butyl-1,2,3,6-tetrahydropyridin-4-yl)-6-chloro-1-(2,6-dichlorophenyl)-2H-quinolizin-2-one (57 mg) in DME was added 2-chlorophenylboronic acid (38 mg), palladium tetrakis triphenylphosphine (14 mg) and 2N sodium carbonate (0.36 mL). The mixture was heated to 80° C. for a couple of hours, then cooled to room temperature, and diluted with ethyl acetate/saturated aqueous sodium bicarbonate. The organic layers were dried over magnesium sulfate and concentrated. The residue was purified by silica gel (100% acetone). The free base was dissolved in methylene chloride and 3 eq. of HCl (1N in ethyl ether) was added to give the HCl salt (26 mg).
$^1$H NMR (CD$_3$OD, 500 MHz) as a free base: δ 7.70 (d, 1H), 7.64 (d, 1H), 7.61 (td, 1H), 7.57-7.49 (m, 4H), 7.34 (t, 1H), 7.23 (dd, 1H), 7.14 (m, 1H), 6.87 (d, 1H), 6.66 (d, 1H), 3.37 (s, 2H), 2.77 (m, 2H), 2.29 (s, 2H), 1.12 (s, 9H). MS (ES): 537.1 (M+H).

EXAMPLE 20

8-(1-tert-butylpiperidin-4-yl)-6-(2-chlorophenyl)-1-(2,6-dichlorophenyl)-2H-quinolizin-2-one

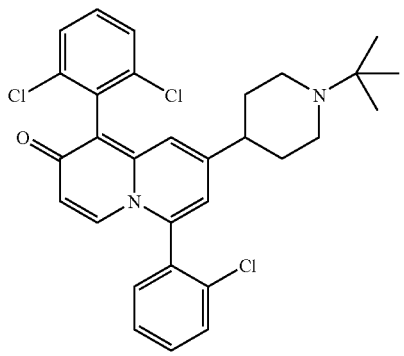

A solution of 8-(1-tert-butyl-1,2,3,6-tetrahydropyridin-4-yl)-6-(2-chlorophenyl)-1-(2,6-dichlorophenyl)-2H-quinolizin-2-one hydrochloride (Example 19, 24 mg) in methanol/ethyl acetate=1/5 was added platinum oxide (9 mg). The solution was hydrogenated under hydrogen (1 atm) for 1 h. The mixture was filtered though celite and concentrated. The residue was purified by silica gel (methylene chloride/methanol/2N ammonia=10/1/0.2) to give the title compound.
$^1$H NMR (CD$_3$OD, 500 MHz): δ 7.92 (d, 1H), 7.72-7.58 (m, 6H), 7.47 (t, 1H), 6.91 (s, 1H), 6.83 (d, 1H), 6.67 (s, 1H), 3.32 (m, 2H), 2.57 (m, 1H), 2.30 (m, 2H), 1.89 (m, 2H), 1.60 (m, 2H), 1.1 (s, 9H).

EXAMPLE 21

8-(1-tert-butylpiperidin-4-yl)-1-(2,6-dichlorophenyl)-6-(2,4-difluorophenyl)-2H-quinolizin-2-one

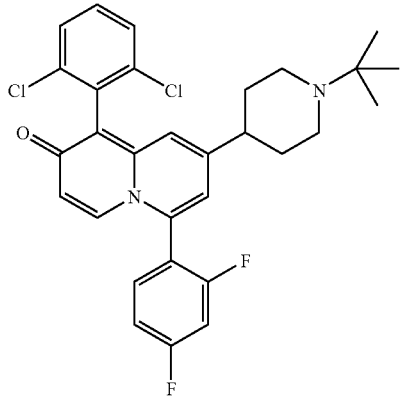

The title compound was prepared by the procedure described in Examples 19 and 20 using 2,4-difluorophenylboronic acid instead of 2-chlorophenylboronic acid in Example 19.
$^1$H NMR (CD$_3$OD, 500 MHz): δ 8.15 (dd, 1H), 7.71 (m, 1H), 7.59 (m, 2H), 7.47 (t, 1H), 7.30 (m, 2H), 6.95 (s, 1H), 6.85 (d, 1H), 6.68 (s, 1H), 3.47 (m, 2H), 2.76 (m, 3H), 2.07 (m, 2H), 1.73 (m, 2H), 1.29 (s, 9H). MS (ES): 541.4 (M+H).

EXAMPLE 22

8-(1-tert-butyl-1,2,3,6-tetrahydropyridin-4-yl)-1-(2,6-dichlorophenyl)-6-(4-fluoro-2-methylphenyl)-2H-quinolizin-2-one hydrochloride

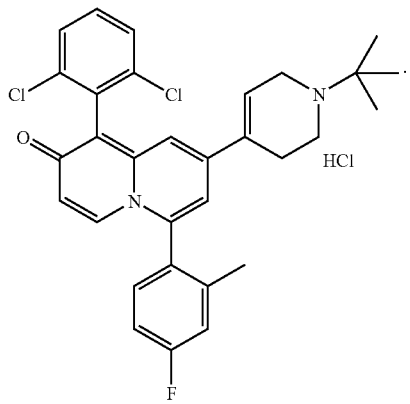

The title compound was prepared by the procedure described in Example 19 using 4-fluoro-2-methylphenylboronic acid instead of 2-chlorophenylboronic acid.

$^1$H NMR (CD$_3$OD, 500 MHz) as a free base: δ 7.90 (d, 1H), 7.59 (d, 2H), 7.47 (m, 2H), 7.23 (m, 2H), 7.13 (s, 1H), 6.80 (d, 1H), 6.66 (s, 1H), 6.56 (s, 1H), 3.41 (s, 2H), 2.81 (m, 2H), 2.32 (s, 2H), 2.14 (s, 3H), 1.12 (s, 9H). MS (ES): 535.5 (M+H).

EXAMPLE 23

8-(1-tert-butylpiperidin-4-yl)-1-(2,6-dichlorophenyl)-6-(4-fluoro-2-methylphenyl)-2H-quinolizin-2-one Hydrochloride

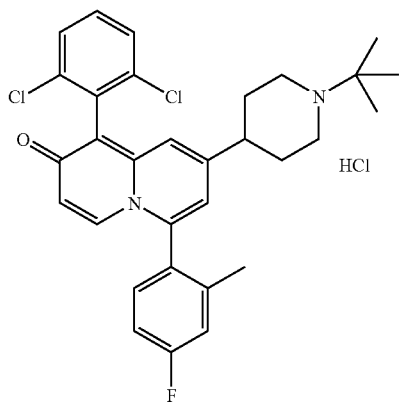

The title compound was prepared by the procedure described in Example 20 from 8-(1-tert-butyl-1,2,3,6-tetrahydropyridin-4-yl)-1-(2,6-dichlorophenyl)-6-(4-fluoro-2-methylphenyl)-2H-quinolizin-2-one hydrochloride (Example 22).

$^1$H NMR (CD$_3$OD, 500 MHz) as a free base: δ 7.91 (d, 1H), 7.54-7.46 (m, 2H), 7.28-7.13 (m, 5H), 6.87 (d, 1H), 6.81 (s, 1H), 3.22 (m, 2H), 2.63 (m, 1H), 2.30 (m, 2H), 2.16 (s, 3H), 1.92 (m, 2H), 1.63 (m, 2H), 1.14 (s, 9H).

EXAMPLE 24

8-(1-tert-butylpiperidin-4-yl)-6-(2-chloro-4-fluorophenyl)-1-(2,6-dichlorophenyl)-2H-quinolizin-2-one

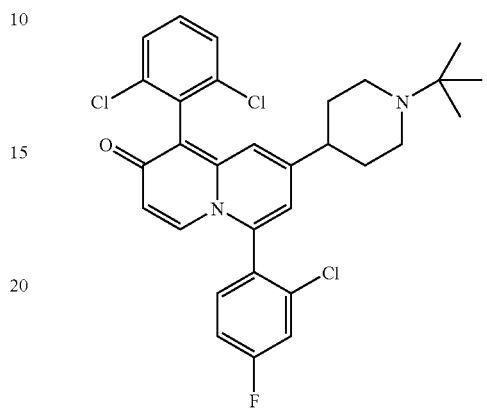

The title compound was prepared by the procedure described in Examples 19 and 20 using 2-chloro-4-fluorophenylboronic acid instead of 2-chlorophenylboronic acid in Example 19.

$^1$H NMR (CD$_3$OD, 500 MHz): δ 7.97 (d, 1H), 7.73 (dd, 1H), 7.59 (m, 2H), 7.47 (t, 1H), 7.40 (m, 2H), 6.97 (s, 1H), 6.84 (d, 1H), 6.69 (s, 1H), 3.48 (m, 2H), 2.82 (m, 3H), 2.07 (m, 2H), 1.81 (m, 2H), 1.30 (s, 9H).

EXAMPLE 25

Preparation of Intermediate 8-(1-tert-butyl-1,2,3,6-tetrahydropyridin-4-yl)-6-chloro-1-(2,6-difluorophenyl)-2H-quinolizin-2-one

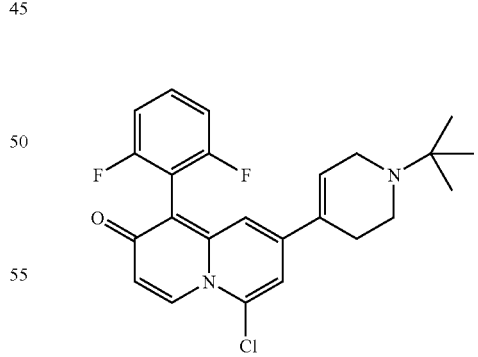

The title compound was prepared by the procedure described in Examples 17 and 18 using 2,6-difluorophenylacetic acid instead of 2,6-dichlorophenylacetic acid in Example 17 Step B.

MS (ES): 429.3 (M+H).

EXAMPLE 26

8-(1-tert-butyl-1,2,3,6-tetrahydropyridin-4-yl)-6-(2-chlorophenyl)-1-(2,6-difluorophenyl)-2H-quinolizin-2-one

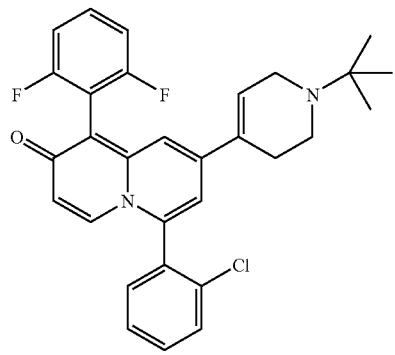

The title compound was prepared by the procedure described in Example 19.

$^1$H NMR (CD$_3$OD, 500 MHz): δ 7.88 (d, 1H), 7.70-7.52 (m, 5H), 7.16 (m, 3H), 6.93 (s, 1H), 6.79 (d, 1H), 6.58 (s, 1H), 3.39 (s, 2H), 2.79 (m, 2H), 2.34 (s, 2H), 1.13 (s, 9H). MS (ES): 505.2 (M+H).

EXAMPLE 27

8-(1-tert-butylpiperidin-4-yl)-6-(2-chlorophenyl)-1-(2,6-difluorophenyl)-2H-quinolizin-2-one

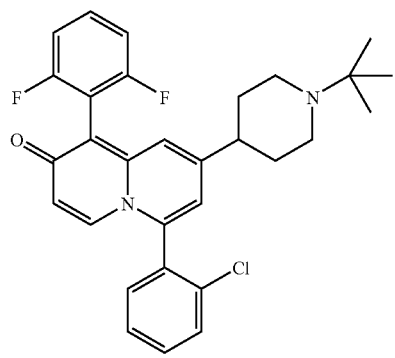

The title compound was prepared by the procedure described in Example 20.

$^1$H NMR (CD$_3$OD, 500 MHz): δ 7.91 (d, 1H), 7.72-7.53 (m, 6H), 7.15 (m, 2H), 6.92 (s, 2H), 6.83 (d, 1H), 3.32 (m, 2H), 2.68 (m, 1H), 2.53 (m, 2H), 1.98 (m, 2H), 1.70 (m, 2H), 1.20 (s, 9H). MS (ES): 507.4 (M+H).

EXAMPLE 28

8-(1-tert-butylpiperidin-4-yl)-6-(2-chloro-4-fluorophenyl)-1-(2,6-difluorophenyl)-2H-quinolizin-2-one

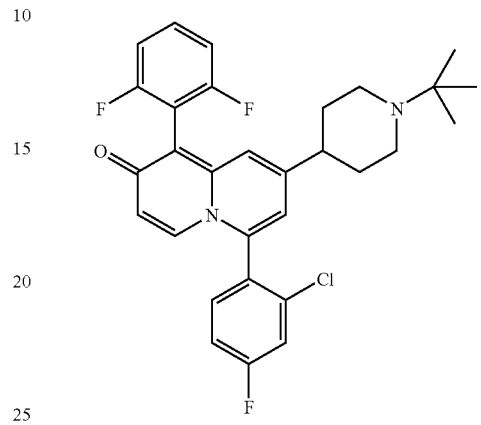

The title compound was prepared by the procedure described in Examples 19 and 20 using 2-chloro-4-fluorophenylboronic acid instead of 2-chlorophenylboronic acid.

$^1$H NMR (CD$_3$OD, 500 MHz): δ 7.96 (d, 1H), 7.70 (dd, 1H), 7.55 (m, 2H), 7.41 (m, 1H), 7.14 (m, 2H), 6.93 (s, 2H), 6.83 (d, 1H), 3.63 (m, 2H), 2.99 (m, 2H), 2.89 (m, 1H), 2.13 (m, 2H), 1.87 (m, 2H), 1.38 (s, 9H). MS (ES): 525.4 (M+H).

EXAMPLES 29

8-(1-tert-butylpiperidin-4-yl)-1-(2,6-difluorophenyl)-6-(4-fluoro-2-methylphenyl)-2H-quinolizin-2-one

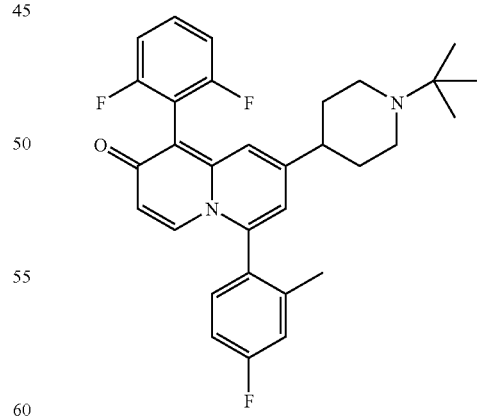

The title compound was prepared by the procedure described in Examples 19 and 20 using 4-fluoro-2-methylphenylboronic acid instead of 2-chlorophenylboronic acid.

MS (ES): 505.4 (M+H).

EXAMPLE 30

3-[6-(2,4-difluorophenyl)-2-oxo-2H-quinolizin-1-yl]-4-fluorobenzonitrile

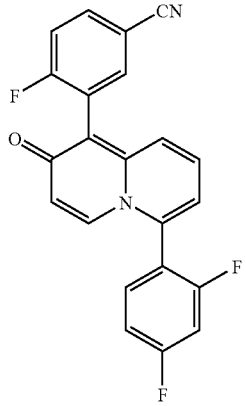

Step-A: 3-(bromomethyl)-4-fluorobenzonitrile

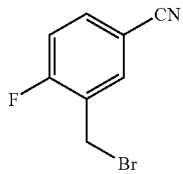

To a solution of 4-fluoro-3-methylbenzonitrile (15.0 g, 111 mmol), in CCl$_4$ (600 mL) was added N-bromosuccinimide (23.7 g, 133 mmol), and benzoyl peroxide (5.38 g, 22.2 mol). The mixture was irradiated with a sunlamp (250 W) to create a gentle reflux. After 0.5 hours of exposure the reaction was complete by TLC. The reaction mixture was cooled and filtered through celite. The filtrate was condensed in vacuo to yield brown oil. The crude residue was purified via silica gel column chromatography (hexanes/ethyl acetate) to yield 17.7 g of the desired product.

$_1$H NMR (CDCl$_3$) δ: 7.78 (d, 1H), 7.65 (m, 1H), 7.20 (t, 1H), 4.48 (s, 2H).

Step-B: 3-[(6-bromopyridin-2-yl)methyl]-4-fluorobenzonitrile

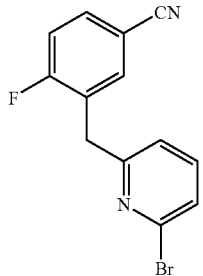

A solution of 3-(bromomethyl)-4-fluorobenzonitrile (from Step A above, 17.7 g, 83.3 mmol) in THF was cooled to 0° C. and then 160 mL of Zn/THF solution (124.4 mmol) was added. After stirring at 0° C. for 45 minutes, the reaction was stirred at ambient temperature for an additional 20 minutes. To this reaction mixture was added 2,6-dibromo pyridine (19.73 g, 83.3 mmol) and tetrakis(triphenylphosphine)palladium (5.00 g, 4.30 mmol), and heated to 90° C. for 1.5 hours until the reaction was complete by TLC. The reaction was cooled to room temperature, filtered through celite, and concentrated. The crude residue was purified via silica gel chromatography (hexanes/methylene chloride) to give the title compound (8.34 g).

$^1$H NMR (CDCl$_3$) δ: 7.82 (d, 1H), 7.68 (m, 1H), 7.42 (t, 1H), 7.26 (d, 1H), 7.20 (t, 1H), 9.96 (d, 1H), 4.18 (s, 2H).

Step-C: 3-{[6-(2,4-difluorophenyl)pyridin-2-yl]methyl}-4-fluorobenzonitrile

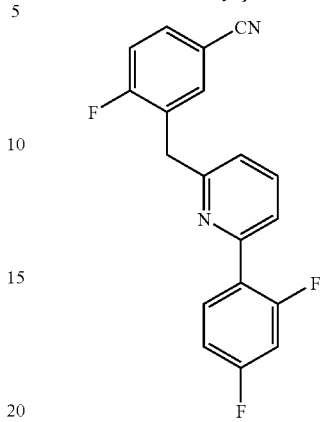

To a solution of 3-[(6-bromopyridin-2-yl)methyl]-4-fluorobenzonitrile (from Step B above, 8.34 g, 28.6 mmol) in toluene (300 mL) was added (2,4-difluorophenyl)boronic acid (8.15 g, 34.4 mmol), tetrakis(triphenylphosphine)palladium (1.65 g, 1.40 mmol), ethanol (30 mL), and 2M Na$_2$CO$_3$ (30 mL). The resulting mixture was heated to 95° C. for 2 hours. The reaction was cooled to room temperature and filtered through celite and concentrated in vacuo. The crude residue was dissolved in EtOAc, washed with H$_2$O, brine (2×), dried over MgSO$_4$, and concentrated. The crude material was purified via silica gel chromatography (hexanes/ethyl acetate) to give the title compound as a white solid (7.03 g).

$^1$H NMR (CDCl$_3$) δ: 8.00 (q, 1H), 7.68 (m, 3H), 7.57 (m, 1H), 7.18 (m, 2H), 7.02 (m, 1H), 6.90 (m, 1H), 4.25 (s, 2H).

Step-D: 3-[1-[6-(2,4-difluorophenyl)pyridin-2-yl]-2-oxo-4-(trimethylsilyl)but-3-yn-1-yl]-4-fluorobenzonitrile

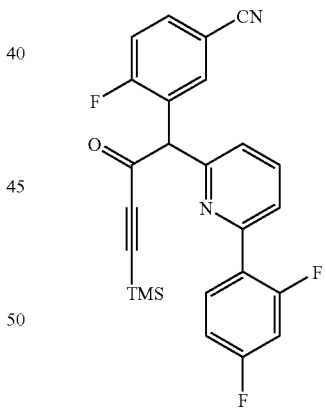

To a solution of 3-{[6-(2,4-difluorophenyl)pyridin-2-yl]methyl}-4-fluorobenzonitrile (from Step C above, 30.0 g, 92.3 mmol) in THF (700 mL) was added LiHMDS (276 mL, 276 mmol, 1M solution in THF) via cannula at −78° C. After stirring for 1 hr and 15 min at −78° C., ethyl 3-(trimethylsilyl)prop-2-ynoate (4.01 mL, 21.37 mmol) was added. The reaction was allowed to stir at −78° C. for 1 hr and was allowed to warm to 0° C. over 3 hours. The reaction was quenched with aqueous NH$_4$Cl, extracted with ethyl acetate (2×). The organic layers were combined, washed with 0.5 N HCl, water, brine (2×), dried over MgSO$_4$, and condensed in vacuo to yield a black oil. The crude material was purified via silica gel chromatography (100% CH$_2$Cl$_2$) to give the title compound (40.0 g).

¹H NMR (CDCl₃) δ: 7.85 (m, 2H), 7.75 (m, 2H), 7.53 (m, 1H), 7.30 (m, 1H), 7.01 (m, 2H), 6.94 (d, 1H), 0.08 (s, 9H).

Step-E: 3-{1-[6-(2,4-difluorophenyl)pyridin-2-yl]-2-oxobut-3-yn-1-yl}-4-fluorobenzonitrile

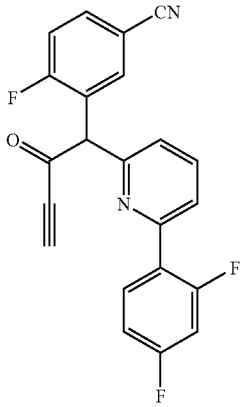

To a solution of 3-[1-[6-(2,4-difluorophenyl)pyridin-2-yl]-2-oxo-4-(trimethylsilyl)but-3-yn-1-yl]-4-fluorobenzonitrile (from Step D above, 40 g, 89.0 mmol) in THF (750 mL) was added TBAF (133 mL, 133.6 mmol) at 0° C. After stirring at 0° C. for 15 min, the reaction was poured into aqueous NH₄Cl, and extracted with EtOAc (2×). The organic layers were combined, washed with H₂O, brine, dried over MgSO₄. The mixture was concentrated and purified by silica gel chromatography (hexanes/methylene chloride) to give title compound (24 g). ¹H NMR (CDCl₃) δ: 7.80 (q, 1H), 7.72 (m, 3H), 7.51 (d, 1H), 7.31 (t, 1H), 7.04 (m, 1H), 6.97 (m, 1H), 6.60 (d, 1H), 3.14 (s, 10H).

Step-F: 3-[6-(2,4-difluorophenyl)-2-oxo-2H-quinolizin-1-yl]-4-fluorobenzonitrile

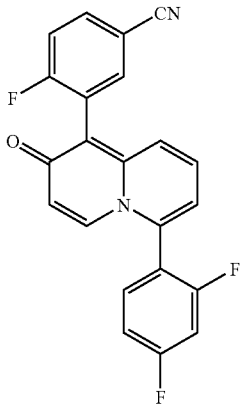

To a solution of 3-{1-[6-(2,4-difluorophenyl)pyridin-2-yl]-2-oxobut-3-yn-1-yl}-4-fluorobenzonitrile (From Step E above, 24 g, 63.8 mmol) in NMP was heated to 90° C. for ½ hour. LCMS analysis revealed the reaction was complete and the reaction was poured into ice water (4 L). After stirring for 12 h, the solid precipitate was collected by filtration. The solid was purified via silica gel chromatography (CH₂Cl₂/EtOAc/MeOH). The aqueous filtrate was extracted with EtOAc. The organic layer was washed with H₂O (4×), brine (2×), dried over MgSO₄, and condensed in vacuo. The crude residue was purified using silica gel chromatography (CH₂Cl₂/EtOAc/MeOH). A combined 7.8 g of the title compound was collected.

¹H NMR (CD₃OD) δ: 8.19 (d, 1H), 7.92 (m, 1H), 7.85-7.79 (m, 1H), 6.60 (m, 1H), 7.50-7.43 (m, 2H), 7.31 (m, 2H), 7.18 (d, 1H), 6.96 (d, 1H), 6.88 (d, 1H).

EXAMPLE 31

3-[6-(2,4-difluorophenyl)-2-oxo-2H-quinolizin-1-yl]-4-fluorobenzoic acid

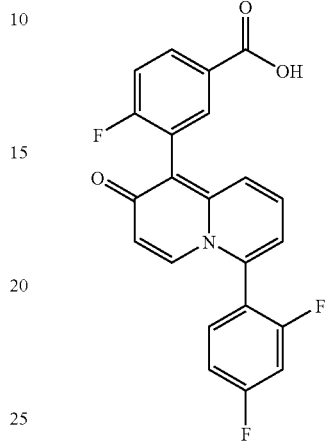

A solution of 3-[6-(2,4-difluorophenyl)-2-oxo-2H-quinolizin-1-yl]-4-fluorobenzonitrile (Example 30, 7.8 g, 19.7 mmol) in dioxane (200 mL) and 2N KOH (200 mL) was heated to 60° C. for 16 hours and 70° C. for 4 hours before the reaction was complete via LCMS. All solvents were removed in vacou and the crude residue was dissolved in H₂O. The aqueous layer was extracted with ether. The organic layer was discarded. The aqueous layer was acidified by 1N HCl to pH 3.5-4.0 and solid precipitation was formed. The aqueous solution was stirred for 12 h at room temperature and the solid precipitate was collected by filtration. The solid was washed with water dried under air to give the title compound (6.67 g).

¹H NMR (CD₃OD) δ: 8.79 (m, 1H), 8.23 (m, 1H), 8.04 (m, 1H), 7.84 (m, 1H), 7.72 (m, 1H), 7.50 (m, 2H), 7.40-7.32 (m, 4H).

EXAMPLE 32

Methyl 3-[6-(2,4-difluorophenyl)-2-oxo-2H-quinolizin-1-yl]-4-fluorobenzoate

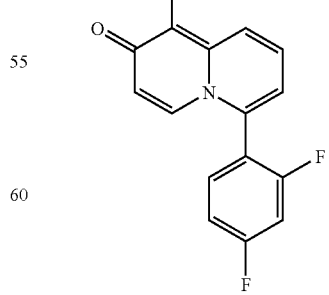

To a solution of 3-[6-(2,4-difluorophenyl)-2-oxo-2H-quinolizin-1-yl]-4-fluorobenzoic acid (Example 31, 15 mg, 0.04 mmol) in MeOH (2 mL) was added oxalyl chloride dropwise at 0° C. The reaction mixture was allowed to warm to ambient temperature for 12 h. The mixture was concentrated and the crude material was purified via silica gel chromatography (100% EtOAc).

$^1$H NMR (CD$_3$OD) δ: 8.19 (d, 2H), 8.07-8.02 (m, 1H), 7.67 (m, 1H), 7.41 (m, 2H), 7.37 (m, 2H), 7.17 (d, 1H), 6.96 (d, 1H), 6.89 (d, 1H), 3.91 (s, 3H).

EXAMPLE 33

3-[6-(2,4-difluorophenyl)-2-oxo-2H-quinolizin-1-yl]-4-fluorobenzamide

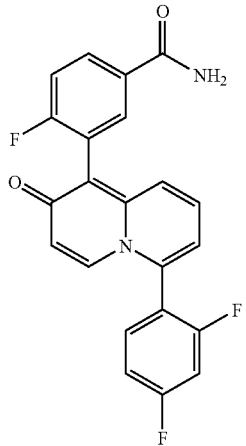

To a solution of 3-[6-(2,4-difluorophenyl)-2-oxo-2H-quinolizin-1-yl]-4-fluorobenzonitrile (Example 30) in dioxane/2N KOH was heated to 60° C. for 1 h. The solution was concentrated and purified via reverse phase HPLC (10-100% acetonitrile in H$_2$O, Kromisil, C8, 30×100 mm) to give a title compound.

$^1$H NMR (CD$_3$OD) δ: 8.80 (m, 1H), 8.11 (m, 1H), 7.90 (m, 2H), 7.73 (m, 1H), 7.61 (d, 1H), 7.50 (d, 1H), 7.44 (m, 1H), 7.33 (m, 3H).

EXAMPLE 34

6-(2,4-difluorophenyl)-1-[2-fluoro-5-(5-methyl-1,3,4-oxadiazol-2-yl)phenyl]-2H-quinolizin-2-one

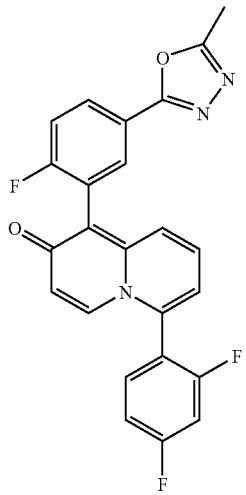

A solution of 3-[6-(2,4-difluorophenyl)-2-oxo-2H-quinolizin-1-yl]-4-fluorobenzoic acid (Example 31, 1.0 g, 2.53 mmol) in CH$_2$Cl$_2$ (20 mL) was added triethyl amine (511 mg, 5.06 mmol) and ethylchloroformate (409 mg, 3.79 mmol) at 0° C. The mixture was warmed to ambient temperature and allowed to stir for an additional 1 h. The reaction was quenched with aqueous NH$_4$Cl, extracted with CH$_2$Cl$_2$ and washed with 0.5 N HCl (1×), brine, dried over MgSO$_4$, and concentrated in vacou. The crude mixture was dissolved in CH$_2$Cl$_2$ and was added to a hydrazine solution (25.3 mmol of hydrazine in 10 mL CH$_2$Cl$_2$) via cannula. After stirring for 10 min at room temperature, the reaction was concentrated in vacuo to yield a solid. The crude solid was washed with MeOH and ether/EtOAc (1/1) to remove impurity. The resulting solid was added MeOH (5 mL) and trimethyl orthoacetate (20 mL) and heated to 110° C. for 2 hrs. LCMS revealed the reaction was complete and the mixture was concentrated in vacuo. The crude material was purified via silica gel chromatography (CH$_2$Cl$_2$/EtOAc/MeOH) to give the title compound as a yellowish solid (450 mg).

$^1$H NMR (CD$_3$OD) δ: 8.19 (m, 2H), 8.07 (m, 1H), 7.68 (m, 1H), 7.49 (m, 1H), 7.41 (m, 1H), 7.33 (m, 2H), 7.21 (d, 1H), 6.91 (d, 1H), 6.89 (d, 1H), 2.62 (s, 3H).

EXAMPLE 35

6-(2,4-difluorophenyl)-1-[2-fluoro-5-(1,3,4-oxadiazol-2-yl)phenyl]-2H-quinolizin-2-one

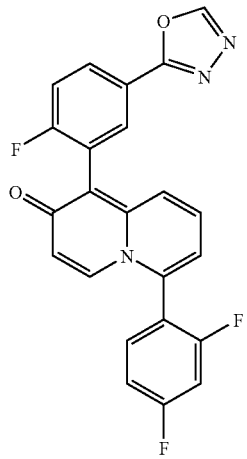

To a solution of 3-[6-(2,4-difluorophenyl)-2-oxo-2H-quinolizin-1-yl]-4-fluorobenzoic acid (Example 31, 400 mg, 1.01 μmol) in CH$_2$Cl$_2$ (5 mL) was added oxalyl chloride (190 mg, 1.50 mmol), and a catalytic amount of DMF at 0° C. After 15 minutes at 0° C. the ice bath was removed and the reaction warmed to ambient temperature. LCMS revealed the reaction was complete and all volatile material was removed in vacuo. The crude residue was dissolved in CH$_2$Cl$_2$ and was added to a hydrazine solution (10.1 mmol of hydrazine in 3 mL CH$_2$Cl$_2$) via cannula. After stirring for 10 min, the reaction was concentrated in vacuo to yield a solid. The crude material was dissolved in MeOH (1 mL) and triethyl orthoformate (4 mL) and heated to 120° C. for 1.5 hours. LCMS revealed the reaction was complete and the mixture was concentrated in vacuo. The crude material was purified via silica gel chromatography (CH$_2$Cl$_2$/EtOAc/MeOH) to give the title compound as a yellowish solid (46 mg).

$^1$H NMR (CD$_3$OD) δ: 9.01 (d, 1H), 8.24 (m, 1H), 8.20 (dd, 1H), 8.13 (m, 1H), 7.70 (m, 1H), 7.52 (m, 1H), 7.44 (m, 1H), 7.33 (m, 2H), 7.22 (d, 1H), 6.97 (d, 1H), 6.90 (d, 1H).

EXAMPLE 36

6-(2,4-difluorophenyl)-1-[2-fluoro-5-(3-methyl-1,2,4-oxadiazol-5-yl)phenyl]-2H-quinolizin-2-one

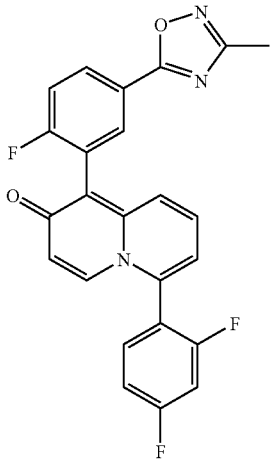

To a solution of 3-[6-(2,4-difluorophenyl)-2-oxo-2H-quinolizin-1-yl]-4-fluorobenzoic acid (Example 31, 50 mg, 0.12 mmol) in acetonitrile (1.2 mL) was added EDC (48 mg, 0.25 mmol), and HOBt (34 mg, 0.25 mmol). The reaction was stirred at room temperature for 1 hour and then N-hydroxyethanimidamide (46.6 mg, 0.63 mmol) was added. The reaction was heated to 90° C. for 18 hours and then cooled to room temperature. The mixture was diluted with EtOAc washed with aqueous NH$_4$Cl, 0.5 N HCl, water, brine, dried over MgSO$_4$, and concentrated. The crude material was purified via silica gel chromatography (100% EtOAc to give the title compound as a light yellow solid (15 mg).

$^1$H NMR (CD$_3$OD) δ: 8.28 (m, 1H), 8.20 (d, 1H), 8.15 (m, 1H), 7.68 (m, 1H), 7.50 (m, 1H), 7.42 (m, 1H), 7.30 (m, 2H), 7.22 (d, 1H), 6.98 (d, 1H), 6.90 (d, 1H), 2.43 (s, 3H).

EXAMPLE 37

4-[6-(2,4-difluorophenyl)-2-oxo-2H-quinolizin-1-yl]-3,5-difluorobenzonitrile

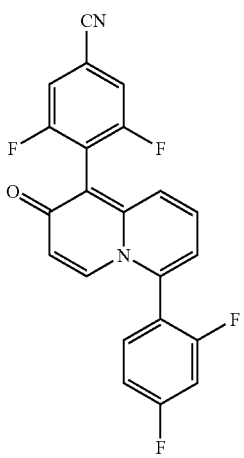

Step-A: 4-bromo-2,6-difluorobenzyl methanesulfonate

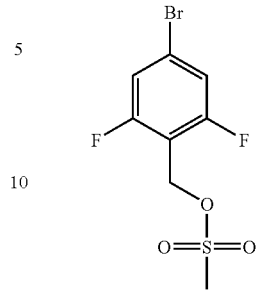

To a solution of (4-bromo-2,6-difluorophenyl)methanol (24.8 g, 112.1 mmol) in CH$_2$Cl$_2$ (400 mL) was added TEA (22.68 g, 224.28 mmol) and methylsulfonyl chloride (12.84 mL, 156.9 mmol) at 0° C. The reaction was stirred at 0° C. for 1 h, quenched with aqueous NH$_4$Cl, and diluted with EtOAc. The organic layer was washed with 1N HCl (2×), H$_2$O, brine, dried over MgSO$_4$, and condensed to give the desired compound.

$^1$H NMR (CDCl$_3$) δ: 7.20 (d, 2H), 5.28 (s, 2H), 3.08 (s, 3H).

Step-B: 5-bromo-2-(bromomethyl)-1,3-difluorobenzene

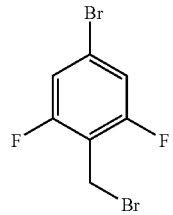

To a solution of 4-bromo-2,6-difluorobenzyl methanesulfonate (from Step A above) in DMF (400 mL) was added LiBr (28.8 g, 335 mmol) and heated to 90° C. for 45 minutes. The reaction was cooled to room temperature and diluted with EtOAc. The organic layer was washed with water (5×), brine (2×) dried over MgSO$_4$, and concentrated in vacuo to yield a brown oil. The crude residue was purified via silica gel column chromatography (CH$_2$Cl$_2$/hexanes) to yield the title compound (24 g).

$^1$H NMR (CDCl$_3$) δ: 7.14 (d, 2H), 4.48 (s, 2H).

Step-C: 2-bromo-6-(4-bromo-2,6-difluorobenzyl)pyridine

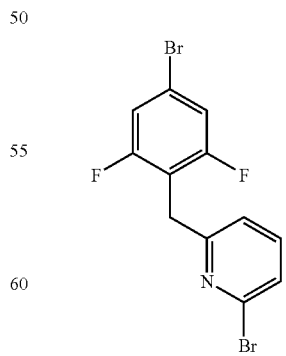

To a solution of 5-bromo-2-(bromomethyl)-1,3-difluorobenzene (from Step B above, 18.5 g, 65.17 mmol) in THF (400 mL) was added 100 mL of Zn/THF solution (5 g Zn/100 mL, 76.46 mmol) at 0° C. The mixture was warmed to room temperature and stirred for 30 minutes. To this reaction was added 2,6-dibromo pyridine (15.44 g, 65.17 mmol) and tetrakis(triphenylphosphine)palladium (7.51 g, 6.51 mmol), and heated to 90° C. for 1 hr. The reaction was monitor by LCMS. After cooling to room temperature, the reaction was quenched with aqueous NH₄Cl, and diluted with EtOAc. The organic layer was washed with water (3×), brine (3×), dried over MgSO₄, and condensed in vacuo to yield a yellow oil. The crude residue was purified via silica gel chromatography to give the title compound (16 g).

¹H NMR (CDCl₃) δ: 7.44 (t, 1H), 7.34 (d, 1H), 7.11 (d, 2H), 6.98 (d, 1H), 4.14 (s, 2H).

Step-D: 2-(4-bromo-2,6-difluorobenzyl)-6-(2,4-difluorophenyl)pyridine

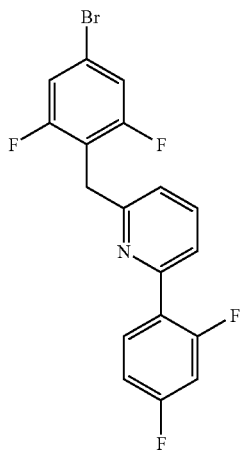

To a solution of 2-bromo-6-(4-bromo-2,6-difluorobenzyl)pyridine (from Step C above, 7.41 g, 20.53 mmol) in toluene (200 mL) was added (2,4-difluorophenyl)boronic acid (3.89 g, 24.63 mmol), tetrakis(triphenylphosphine)palladium (2.37 g, 2.05 mmol), ethanol (20 mL) and 2M Na₂CO₃ (20 mL). The reaction was heated to 90° C. until complete. The mixture was cooled to room temperature and concentrated. The crude residue was diluted with EtOAc/water (1:1) and washed with 1N HCl (2×), brine (3×), dried over MgSO₄, and concentrated in vacuo. The crude material was purified via silica gel chromatography (hexanes/ethyl acetate) to give the title compound (7.23 g).

¹H NMR (CDCl₃) δ: 8.09 (q, 1H), 7.66 (m, 2H), 7.14 (m, 3H), 7.01 (m, 1H), 6.90 (m, 1H), 4.26 (s, 2H).

Step-E: 4-{[6-(2,4-difluorophenyl)pyridin-2-yl]methyl}-3,5-difluorobenzonitrile

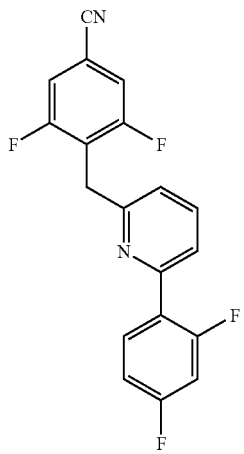

To a solution of 2-(4-bromo-2,6-difluorobenzyl)-6-(2,4-difluorophenyl)pyridine (from Step D above, 7.32 g, 18.5 mmol) in wet DMF (200 mL of DMF and 2 mL water) was added Zn(CN)₂ (1.74 g, 14.8 mmol), tris(dibenzylideneacetone)dipalladium (842 mg, 0.92 mmol), and 1,1'-bis(diphenylphosphino)ferrocene (1.23 g, 2.22 mmol) and heated to 120° C. for 1 hr (monitored via LCMS). After the reaction cooled to ambient temperature, the mixture was diluted with H₂O and extracted with EtOAc (3×). The combined organic layers were washed with water (4×), brine (3×), dried over MgSO₄, and condensed in vacuo. The crude material was purified via silica gel chromatography (hexanes/ethyl acetate) to give the title compound (6.1 g).

¹H NMR (CDCl₃) δ: 7.95 (q, 1H), 7.70 (m, 2H), 7.28 (m, 2H), 7.16 (d, 1H), 6.99 (m, 1H), 6.90 (m, 1H), 4.33 (s, 2H).

Step-F: 4-[1-[6-(2,4-difluorophenyl)pyridin-2-yl]-2-oxo-4-(trimethylsilyl)but-3-yn-1-yl]-3,5-difluorobenzonitrile

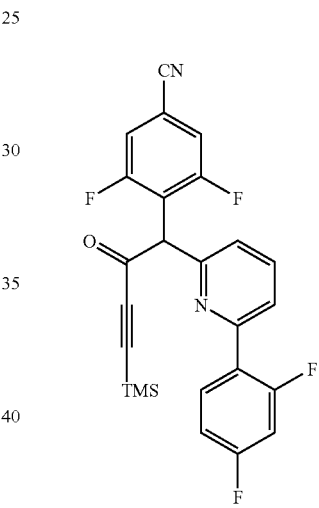

To a solution of 4-{[6-(2,4-difluorophenyl)pyridin-2-yl]methyl}-3,5-difluorobenzonitrile (from Step E above, 6.10 g, 17.83 mmol) in THF (200 mL) was added lithium bis(trimethylsilyl)amide (53.49 mL, 1.0 M in THF) at −78° C. After stirring 1¼ h at −78° C., ethyl 3-(trimethylsilyl)prop-2-ynoate (4.01 mL, 21.37 mmol) was added to the reaction mixture. The reaction continued to stir at −78° C. for 1 hr and was warmed to −20° C. until the reaction was complete via LMCS. The reaction was quenched with aqueous NH₄Cl and extracted with EtOAc (3×). The combined organic layers were washed with 1N HCl (1×), water, brine, dried over MgSO₄, and condensed. The crude material was purified via silica gel chromatography (hexanes/methylene chloride) to give the title compound (7.0 g).

¹H NMR (CDCl₃) δ: 7.87 (q, 1H), 7.74 (t, 1H), 7.53 (d, 1H), 7.35 (m, 2H), 7.07 (m, 1H), 7.01 (t, 1H), 6.61 (d, 1H), 0.08 (s, 9H).

Step-G: 4-{1-[6-(2,4-difluorophenyl)pyridin-2-yl]-2-oxobut-3-yn-1-yl}-3,5-difluorobenzonitrile

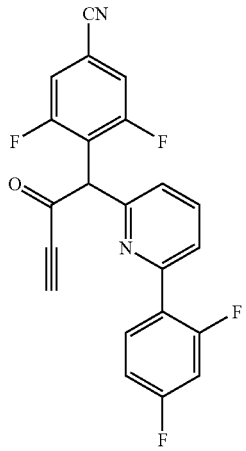

To a solution of 4-[1-[6-(2,4-difluorophenyl)pyridin-2-yl]-2-oxo-4-(trimethylsilyl)but-3-yn-1-yl]-3,5-difluorobenzonitrile (from Step F above, 7.00 g, 15.02 mmol) in THF (200 mL) was added tetrabutylammonium fluoride hydrate (22.5 mL, 1.0 M in THF) at 0° C. After stirring at 0° C. for 10 min, the reaction was diluted with EtOAc (3×), washed with aqueous NH$_4$Cl, H$_2$O, brine, dried over MgSO$_4$ and concentrated. The crude residue was purified using silica gel chromatography (hexanes/methylene chloride) to yield the title compound (5.31 g).

$^1$H NMR (CDCl$_3$) δ: 7.86 (m, 1H), 7.76 (m, 1H), 7.54 (d, 1H), 7.35 (m, 2H), 7.08 (m, 1H), 7.01 (m, 1H), 6.61 (d, 1H), 3.12 (s, 1H).

Step-H: 4-[6-(2,4-difluorophenyl)-2-oxo-2H-quinolizin-1-yl]-3,5-difluorobenzonitrile

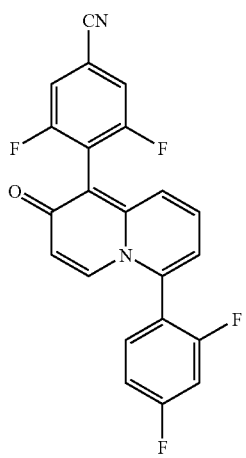

To a solution of 4-{1-[6-(2,4-difluorophenyl)pyridin-2-yl]-2-oxobut-3-yn-1-yl}-3,5-difluorobenzonitrile (from Step G above, 2.4 g, 6.07 mmol) in tetramethylethyldiamine was heated to 110° C. until reaction completed. The mixture was concentrated and purified via silica gel chromatography (CH$_2$Cl$_2$/EtOAc) to give the title compound as a yellow solid (0.91 g). $^1$H NMR (CD$_3$OD) δ: 8.21 (d, 1H), 7.69 (m, 1H), 7.61 (m, 2H), 7.49 (m, 1H), 7.31 (m, 2H), 7.18 (d, 1H), 6.99 (d, 1H), 6.89 (d, 1H).

EXAMPLE 38

4-[6-(2,4-difluorophenyl)-2-oxo-2H-quinolizin-1-yl]-3,5-difluorobenzoic acid

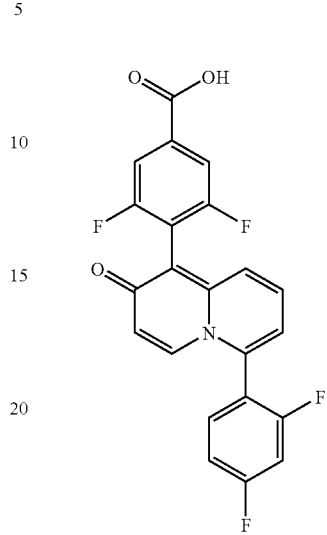

To a solution of 4-[6-(2,4-difluorophenyl)-2-oxo-2H-quinolizin-1-yl]-3,5-difluorobenzonitrile (Example 37, 400 mg, 1.02 mmol) in dioxane (50 mL) and 2 N KOH (50 mL) was heated to 90° C. for 24 hours (monitor by LCMS). All solvents were removed in vacuo and the crude residue was dissolved in water. The aqueous layer was extracted with ether (3×) and the ether layers were discarded. The aqueous layer was acidified with 1 N HCl to pH 4 to give solid precipitation. The solid was collected by filtration and washed with H$_2$O to give the title compound (350 mg).

$^1$H NMR (CD$_3$OD) δ: 8.25 (d, 1H), 7.75 (m, 2H), 7.68 (m, 1H), 7.52 (m, 1H), 7.30 (m, 2H), 7.22 (d, 1H), 7.05 (d, 1H), 6.96 (d, 1H).

EXAMPLE 39

1-[2,6-difluoro-4-(1,3,4-oxadiazol-2-yl)phenyl]-6-(2,4-difluorophenyl)-2H-quinolizin-2-one

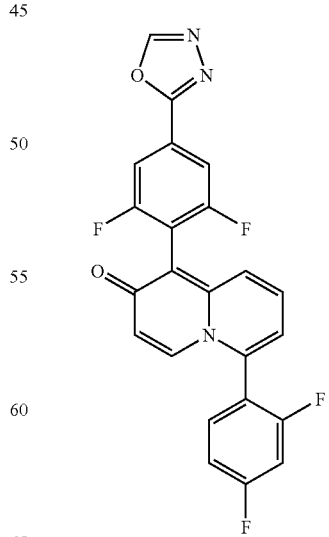

To a solution of 4-[6-(2,4-difluorophenyl)-2-oxo-2H-quinolizin-1-yl]-3,5-difluorobenzoic acid (Example 38, 152 mg, 0.37 mmol) in CH$_2$Cl$_2$ (3.7 mL) was added oxalyl chloride (0.047 mL, 0.55 mmol) and a catalytic amount of DMF at 0° C. After stirring for 10 min at 0° C., the mixture warmed to ambient temperature. LCMS analysis revealed the reaction was complete and the reaction was concentrated in vacuo. The residue in CH$_2$Cl$_2$ (3.7 mL) was added to a hydrazine solution (0.1 mL hydrazine in 1 mL CH$_2$Cl$_2$) via cannula. After stirring for 10 min at room temperature, the reaction was complete and concentrated in vacuo to yield a solid which was added methanol (1 mL) and triethyl orthoformate (2 mL) and heated to 110° C. for 2 hrs. LCMS revealed the reaction was complete and all volatile material was removed in vacuo. The crude material was purified via reverse phase chromatography and silica gel chromatography (CH$_2$Cl$_2$/EtOAc/MeOH) to give the title compound as a yellowish solid (10 mg).

$^1$H NMR (CD$_3$OD) δ: 9.11 (s, 1H), 8.21 (d, 1H), 7.85 (m, 2H), 7.68 (m, 1H), 7.50 (m, 1H), 7.31 (m, 2H), 7.22 (d, 1H), 7.00 (d, 1H), 6.89 (d, 1H).

EXAMPLE 40

1-[2,6-difluoro-4-(5-methyl-1,3,4-oxadiazol-2-yl)phenyl]-6-(2,4-difluorophenyl)-2H-quinolizin-2-one

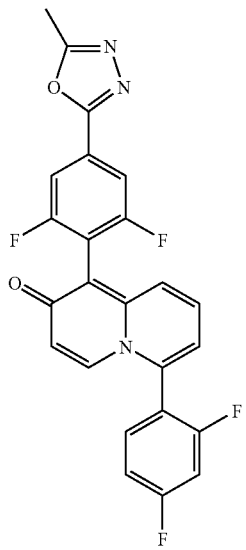

To a solution of 4-[6-(2,4-difluorophenyl)-2-oxo-2H-quinolizin-1-yl]-3,5-difluorobenzoic acid (Example 38, 204 mg, 0.49 mmol) in CH$_2$Cl$_2$ (1.5 mL) was added oxalyl chloride (93 mg, 0.74 mmol) and a catalytic amount of DMF at 0° C. After stirring at 0° C. for 5 min, the reaction was warmed to room temperature and stirred an additional for 30 min. The reaction was concentrated in vacuo and azeotrophed with toluene (2×). The crude material was dissolved in CH$_2$Cl$_2$ (1.5 mL) and was added to a solution of hydrazine (50 mmol) in CH$_2$Cl$_2$ (2 mL) at 0° C. After stirring for 15 min, the reaction was complete via LCMS analysis and the reaction was condensed to a solid, and azeotrophed with toluene (2×). The crude material was dissolved in trimethyl orthoacetate (5 mL) and methanol (2 mL) and heated to 120° C. for 1.5 hours. All volatile material was removed under reduced pressure and the crude material was purified via silica gel chromatography (100% EtOAc).

$^1$H NMR (CD$_3$OD) δ: 8.22 (d, 1H), 7.82 (m, 2H), 7.68 (m, 1H), 7.49 (m, 1H), 7.31 (m, 2H), 7.23 (d, 1H), 7.00 (d, 1H), 6.90 (d, 1H), 2.67 (s, 3H).

EXAMPLE 41

1-[4-(5-amino-1,3,4-oxadiazol-2-yl)-2,6-difluorophenyl]-6-(2,4-difluorophenyl)-2H-quinolizin-2-one

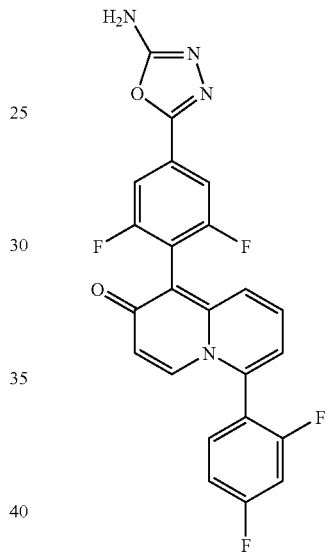

To a solution of 4-[6-(2,4-difluorophenyl)-2-oxo-2H-quinolizin-1-yl]-3,5-difluorobenzoic acid (Example 38, 50 mg, 0.12 mmol) in CH$_2$Cl$_2$ was added oxalyl chloride (22 mg, 0.18 mmol) and a catalytic amount of DMF at 0° C. After 10 min the reaction was removed from the ice bath and stirred at room temperature for 20 min. LCMS analysis revealed the reaction was complete and the reaction was concentrated in vacuo. To this crude reside in CH$_2$Cl$_2$ was added to a hydrazine solution (1.2 mmol hydrazine in 1 mL CH$_2$Cl$_2$) at 0° C. via cannula. After 10 min at 0° C. the reaction was allowed to warm to room temperature. The reaction was concentrated in vacuo to yield a solid which was added methanol (1 mL) and cyanogen bromide (126 mg, 1.2 mmol) and heated to 90° C. for 2 hrs. LCMS revealed the reaction was complete and the mixture was concentrated in vacuo. The crude material was purified via reverse phase chromatography to give the title compound (5.4 mg).

$^1$H NMR (CD$_3$OD) δ: 8.20 (d, 1H), 7.62-7.72 (m, 3H), 7.48 (m, 1H), 7.21-7.34 (m, 2H), 7.21 (d, 1H), 7.00 (d, 1H), 6.88 (d, 1H).

EXAMPLE 42

1-[2,6-difluoro-4-(3-methyl-1,2,4-oxadiazol-5-yl)phenyl]-6-(2,4-difluorophenyl)-2H-quinolizin-2-one

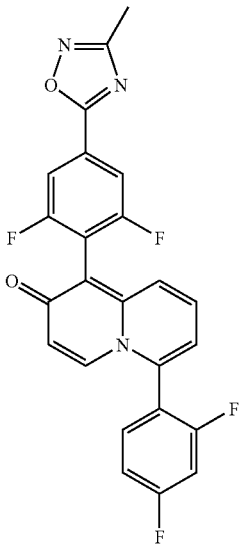

A solution of 4-[6-(2,4-difluorophenyl)-2-oxo-2H-quinolizin-1-yl]-3,5-difluorobenzoic acid (Example 38, 50 mg, 0.12 mmol) in NMP (1.2 mL) was added EDC (46 mg, 0.24 mmol), and HOBT (24 mg, 0.18 mmol) at room temperature. The reaction was stirred at room temperature for 30 minutes before N'-hydroxyethanimidamide was added. The reaction was heated to 90° C. for 6 hours and yielded an 80% conversion of product via LCMS. The reaction was quenched with NH$_4$Cl and extracted with EtOAc (3×). The combined organic layers were washed with 0.5 N HCl, water, brine, dried over MgSO$_4$, and concentrated. The residue was purified via silica gel chromatography (100% EtOAc) to give the title compound (9 mg).

$^1$H NMR (CD$_3$OD) δ: 8.22 (d, 1H), 7.89 (m, 2H), 7.70 (m, 1H), 7.49 (m, 1H), 7.30 (m, 2H), 7.21 (d, 1H), 6.99 (d, 1H), 6.89 (d, 1H), 2.48 (s, 3H).

EXAMPLE 43

4-[6-(2,4-difluorophenyl)-2-oxo-2H-quinolizin-1-yl]-3,5-difluorobenzamide

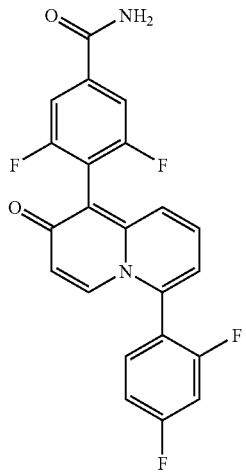

To a solution of 4-[6-(2,4-difluorophenyl)-2-oxo-2H-quinolizin-1-yl]-3,5-difluorobenzoic acid (Example 38) in NMP was added EDC, HOBT and ammonium hydroxide. After reaction complete, the mixture was concentrated and purified by reverse phase chromatography (10-100% ACN in H$_2$O, Kromisil, C8, 30×100 mm) to give the title compound.

$^1$H NMR (CD$_3$OD) δ: 8.21 (d, 1H), 7.68 (m, 3H), 7.45 (m, 1H), 7.31 (m, 2H), 7.17 (d, 1H), 6.99 (d, 1H), 6.88 (d, 1H).

EXAMPLE 44

1-(4-bromo-2,6-difluorophenyl)-6-(2,4-difluorophenyl)-2H-quinolizin-2-one

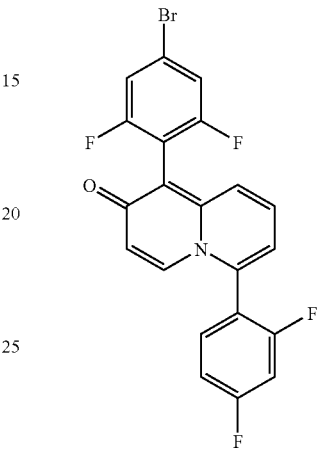

The title compound was prepared by the procedure described in Example 37, Steps F, G and H from 2-(4-bromo-2,6-difluorobenzyl)-6-(2,4-difluorophenyl)pyridine 4-{[6-(2,4-difluorophenyl)pyridin-2-yl]methyl}-3,5-difluorobenzonitrile.

$^1$H NMR (CD$_3$OD) δ: 8.19 (dd, 1H), 7.68 (m, 1H), 7.48 (m, 1H), 7.42 (m, 2H), 7.26-7.34 (m, 2H), 7.18 (d, 1H), 6.90 (d, 1H), 6.88 (d, 1H).

EXAMPLE 45

1-(4-acetyl-2,6-difluorophenyl)-6-(2,4-difluorophenyl)-2H-quinolizin-2-one

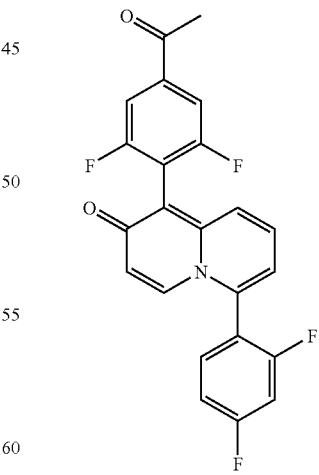

To a solution of 1-(4-bromo-2,6-difluorophenyl)-6-(2,4-difluorophenyl)-2H-quinolizin-2-one (30 mg, 0.067 mmol) in toluene (1.4 mL) was added tributyl(1-ethoxyvinyl)stannane and tetrakis(triphenylphosphine)palladium (7.74 mg, 0.007 mmol) and heated to 90° C. for 1½ h. The reaction was cooled, filtered through celite, and diluted with THF. The mixture was added 2N HCl and stirred for 20 min to complete the reaction. The crude mixture was diluted with H₂O and EtOAc. The organic layer was washed with H₂O, brine, dried over MgSO₄, and condensed. The crude residue was purified via silica gel chromatography (hexanes/ethyl acetate) to give the title compound (7.9 mg).

¹H NMR (CD₃OD) δ: 8.20 (d, 1H), 7.75 (m, 2H), 7.68 (m, 1H), 7.48 (m, 1H), 7.32 (m, 2H), 7.18 (d, 1H), 6.98 (d, 1H), 6.90 (d, 1H), 2.68 (s, 3H).

EXAMPLE 46

4-[6-(2,4-difluorophenyl)-2-oxo-2H-quinolizin-1-yl]-3,5-difluoro-N-methylbenzamide

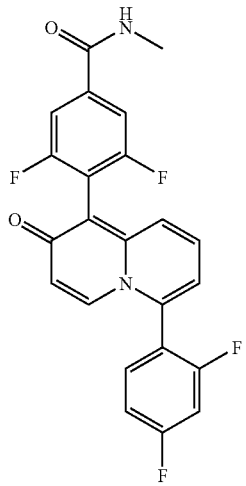

The title compound was prepared by the procedure described in Example 43 using methylamine hydrochloride with 2 equivalents of triethylamine instead of ammonium hydroxide and purified by silica gel (methylene chloride/methanol).

¹H NMR (CD₃OD) δ: 8.20 (d, 1H), 7.69 (m, 1H), 7.61 (m, 2H), 7.48 (m, 1H), 7.31 (m, 2H), 7.17 (d, 1H), 6.98 (d, 1H), 6.88 (d, 1H), 2.96 (s, 3H).

EXAMPLE 47

4-[6-(2,4-difluorophenyl)-2-oxo-2H-quinolizin-1-yl]-3,5-difluoro-N,N-dimethylbenzamide

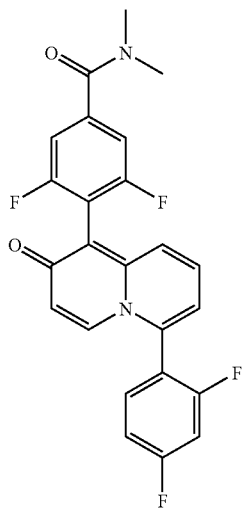

The title compound was prepared by the procedure described in Example 43 using dimethylamine hydrochloride with 2 equivalents of triethylamine instead of ammonium hydroxide and purified by silica gel (methylene chloride/methanol).

¹H NMR (CD₃OD) δ: 8.20 (d, 1H), 7.69 (m, 1H), 7.49 (m, 1H), 7.24 (m, 5H), 6.98 (d, 1H), 6.90 (d, 1H), 2.96 (d, 6H).

EXAMPLE 48

6-(2,4-difluorophenyl)-1-[2,6-difluoro-4-(pyrrolidin-1-ylcarbonyl)phenyl]-2H-quinolizin-2-one

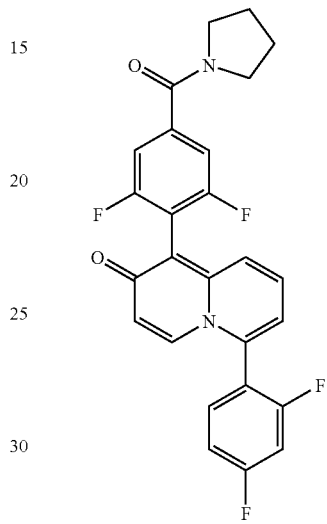

The title compound was prepared by the procedure described in Example 43 using pyrrolidine instead of ammonium hydroxide and purified by silica gel (methylene chloride/methanol).

¹H NMR (CD₃OD) δ: 8.20 (d, 1H), 7.69 (q, 1H), 7.49 (m, 1H), 7.31 (m, 4H), 7.20 (d, 1H), 6.98 (d, 1H), 6.90 (d, 1H), 3.64 (m, 4H), 1.95-2.05 (m, 4H).

EXAMPLE 49

1-(2,6-difluoro-4-pyrimidin-5-ylphenyl)-6-(4-fluorophenyl)-2H-quinolizin-2-one

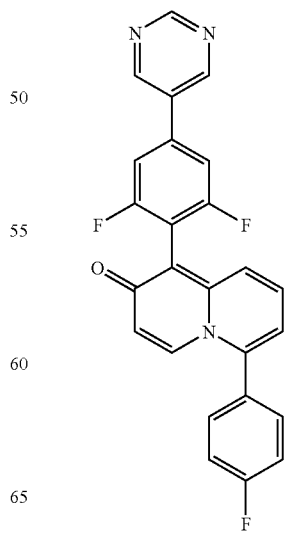

To a solution of 1-(4-bromo-2,6-difluorophenyl)-6-(4-fluorophenyl)-2H-quinolizin-2-one Example 44, 74 mg, 0.17 mmol) in toluene (5 mL) was added pyrimidin-5-ylboronic acid (42 mg, 0.34 mmol), tetrakis(triphenylphosphine)palladium (196 mg, 0.017 mmol), EtOH (0.5 mL) and 2N Na$_2$CO$_3$ (0.5 mL), and heated to 90° C. for 12 h. After cooling the reaction to room temperature, the mixture was concentrated. The crude residue was dissolved in EtOAc and washed with water, brine, dried over MgSO$_4$, and concentrated. The crude material was purified using silica gel chromatography (CH$_2$Cl$_2$/EtOAc/MeOH) to give title compound.

$^1$H NMR (CD$_3$OD) δ: 9.20 (m, 3H), 8.32 (d, 1H), 7.65 (m, 2H), 7.62 (d, 2H), 7.48 (m, 1H), 6.40 (m, 2H), 7.20 (d, 1H), 6.90 (d, 1H), 6.86 (d, 1H).

EXAMPLE 50

6-(2,4-difluorophenyl)-1-(2,6-difluorophenyl)-7-(hydroxymethyl)-2H-quinolizin-2-one

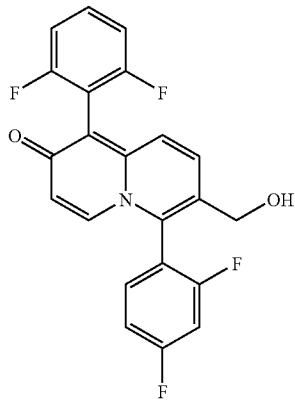

Step-A (2,6-dichloropyridin-3-yl)methanol

To a solution of 2,6-dichloronicotinic acid (10 g) in MeOH (300 mL) was added oxalyl chloride (5.5 mL) dropwise at 0° C. The mixture was heated to 60° C. for a couple of hours until reaction complete. Upon concentration, the residue was dissolved in ether and added lithium aluminum hydride (2.3 g) slowly at 0° C. The reaction was stirred at 0° C. for 1 h and added water (2.3 mL) dropwise to quench excess lithium aluminum hydride. The resulting mixture was added 15% NaOH (2.3 mL) slowly, water (6.9 mL) and stirred at 0° C. for an additional 1 h. The slush solution was filtered through celite and washed with ether. The filtrate was concentrated to give the title compound (6.5 g).

$^1$H NMR (CDCl$_3$) δ: 7.90 (d, 1H), 7.33 (d, 1H), 4.79 (s, 2H).

Step-B 3-({[tert-butyl(dimethyl)silyl]oxy}methyl)-2,6-dichloropyridine

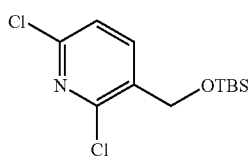

To a solution of (2,6-dichloropyridin-3-yl)methanol (from Step A above, 6.3 g) in DMF was added imidazole (3.06 g) and t-butyldimethylsilyl chloride (6.02 g) at 0° C. The mixture was warmed to room temperature and stirred for 1 h before poured into water. The solution was extracted with ethyl acetate. The organic layer was washed with water (5×), brine, dried over MgSO$_4$ and concentrated. The residue was purified by silica gel (hexanes/ethyl acetate) to give the title compound (8.7 g).

$^1$H NMR (CDCl$_3$) δ: 7.89 (d, 1H), 7.32 (d, 1H), 4.74 (s, 2H), 0.98 (s, 9H), 0.16 (s, 6H).

Step-C 3-({[tert-butyl(dimethyl)silyl]oxy}methyl)-2-chloro-6-(2,6-difluorobenzyl)pyridine

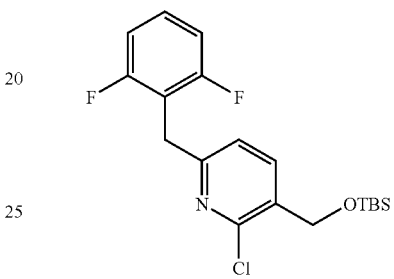

To a solution of 3-({[tert-butyl(dimethyl)silyl]oxy}methyl)-2,6-dichloropyridine (from Step B above, 8.5 g) in THF was added 2,6-difluorobenzylzinc bromide (90 mL, 0.5M in THF) and tetrakis(triphenylphosphine)palladium (2 g), and heated to reflux for a couple of hours until reaction completed. The mixture was cooled to room temperature and filtered through celite. The filtrate was diluted with ethyl acetate, washed with 1N NaOH, brine, dried over MgSO$_4$ and concentrated to give title compound.

Step-D 3-({[tert-butyl(dimethyl)silyl]oxy}methyl)-6-(2,6-difluorobenzyl)-2-(2,4-difluorophenyl)pyridine

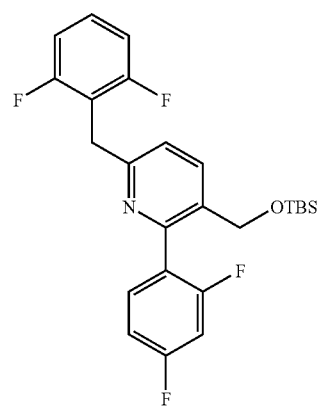

To a crude 3-({[tert-butyl(dimethyl)silyl]oxy}methyl)-2-chloro-6-(2,6-difluorobenzyl)pyridine (from Step C above) in DME was added 2,4-difluorophenylboronic acid (6.5 g), tetrakis(triphenylphosphine)palladium (2 g) and 2N Na$_2$CO$_3$ (40 mL), and heated to 90° C. for a couple of hours until reaction completed. The mixture was cooled to room temperature and filtered through celite. The mixture was diluted with ethyl acetate, washed with water, brine, dried over MgSO$_4$ and concentrated. The residue was purified by silica gel (100% methylene chloride) to give title compound (4.81 g).

MS (ES): 462.3 (M+H).

Step-E 1-(2,6-difluorophenyl)-1-[6-(2,4-difluorophenyl)-5-(hydroxymethyl)pyridin-2-yl]but-3-yn-2-one

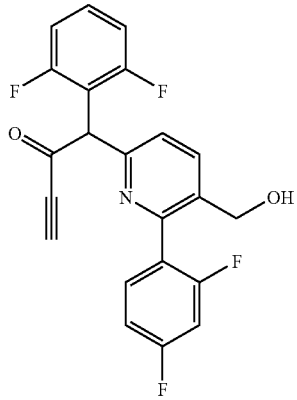

To a solution of 3-({[tert-butyl(dimethyl)silyl]oxy}methyl)-6-(2,6-difluorobenzyl)-2-(2,4-difluorophenyl)pyridine (from Step D above, 4.63 g) in THF was added lithium bis(trimethylsilyl)amide (22.0 mL, 1.0 M in THF) at −78° C. After stirring ½ h at −78° C., ethyl 3-(trimethylsilyl)prop-2-ynoate (2.2 mL) was added. The mixture was warmed to 0° C. and stirred for a couple of hours until reaction complete. The reaction was quenched with 0.1 N HCl, and extracted with ethyl acetate. The organic layer was washed with brine, dried over MgSO$_4$ and concentrated. The residue in THF was added TBAF (25 mL, 1N in THF) at 0° C. and stirred for 1 h. The solution was washed with water, brine, dried over MgSO$_4$ and concentrated. The residue was purified by silica gel (100% methylene chloride) to give title compound (1.08 g).

MS (ES): 400.2 (M+H).

Step-F 6-(2,4-difluorophenyl)-1-(2,6-difluorophenyl)-7-(hydroxymethyl)-2H-quinolizin-2-one

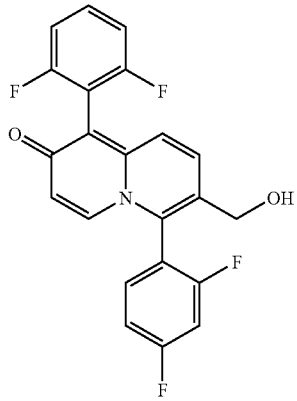

To a solution of 1-(2,6-difluorophenyl)-1-[6-(2,4-difluorophenyl)-5-(hydroxymethyl)pyridin-2-yl]but-3-yn-2-one (from Step E above, 1.0 g) in TMEDA was heated to 110° C. until reaction completed. The mixture was concentrated and purified by silica gel (100% acetone) to give title compound as a yellow solid (0.46 g).

$^1$H NMR (CD$_3$OD) δ: 8.08 (d, 1H), 7.69 (d, 1H), 7.61 (m, 1H), 7.51 (m, 1H), 7.34 (m, 2H), 7.24 (d, 1H), 7.15 (m, 2H), 6.89 (d, 1H), 4.22 (abq, 2H).

MS (ES): 400.2 (M+H).

EXAMPLE 51

6-(2,4-difluorophenyl)-1-(2,6-difluorophenyl)-7-methyl-2H-quinolizin-2-one

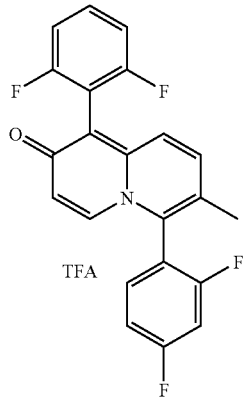

To a solution of 6-(2,4-difluorophenyl)-1-(2,6-difluorophenyl)-7-(hydroxymethyl)-2H-quinolizin-2-one (Example 50, 40 mg) in MeOH was added a catalytic amount of Pd/C under hydrogen atmosphere for 1 h. The mixture was filtered through celite and the filtrate was concentrated. The residue was purified by reverse phase HPLC to give the title compound as a TFA salt (14 mg). $^1$H NMR (CD$_3$OD) δ: 8.58 (d, 1H), 7.93 (d, 1H), 7.66 (m, 3H), 7.40 (m, 3H), 7.25 (m, 2H), 2.23 (s, 2H).

EXAMPLE 52

6-(2,4-difluorophenyl)-1-(2,6-difluorophenyl)-7-(methoxymethyl)-2H-quinolizin-2-one

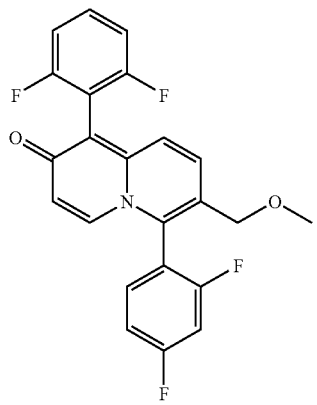

Oil free sodium hydride suspended in THF was added iodomethane (0.06 mL) and 6-(2,4-difluorophenyl)-1-(2,6-difluorophenyl)-7-(hydroxymethyl)-2H-quinolizin-2-one (Example 50, 40 mg) at 0° C. The mixture was warmed to room temperature and stirred for a couple of hours until reaction complete. The mixture was quenched with water, extracted with ethyl acetate, brine, dried over MgSO$_4$ and concentrated. The residue was purified by silica gel (100% acetone) to give the title compound (22 mg).
MS (ES): 414.2 (M+H).

EXAMPLE 53

6-(2,4-difluorophenyl)-1-(2,6-difluorophenyl)-2-oxo-2H-quinolizine-7-carboxylic Acid

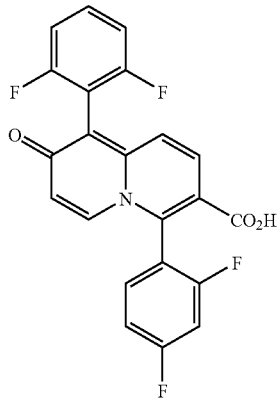

To a solution of 6-(2,4-difluorophenyl)-1-(2,6-difluorophenyl)-7-(hydroxymethyl)-2H-quinolizin-2-one (Example 50, 100 mg) was added Jones reagent (0.5 mL, 4 N in sulfuric acid; prepared using procedure similar to that disclosed in Bowers, Halsall, Jones, and Lemin, *J. Chem. Soc.*, (1953), 2548-2560) at 0° C. The mixture was stirred for a couple of hours at 0° C. until reaction complete and then quenched with isopropanol (1 mL). After stirring for 10 min (green solution), the mixture was filtered through celite and concentrated. The residue was diluted with ethyl acetate and washed with water, brine, dried over MgSO$_4$ and concentrated to give title compound (87 mg).

$^1$H NMR (CD$_3$OD) δ: 8.33 (d, 1H), 8.01 (d, 1H), 7.59 (m, 2H), 7.39 (d, 1H), 7.30 (m, 2H), 7.19 (m, 2H), 7.09 (d, 1H).
MS (ES): 414.2 (M+H).

EXAMPLE 59

4-[6-(2,4-difluorophenyl)-2-oxo-2H-quinolizin-1-yl]-3-fluorobenzoic acid

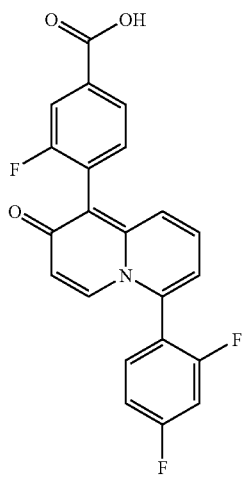

MS (ES): 396.05 (M+H).

EXAMPLE 60

6-(2,4-difluorophenyl)-1-[2-fluoro-4-(1-hydroxy-1-methylethyl)phenyl]-2H-quinolizin-2-one

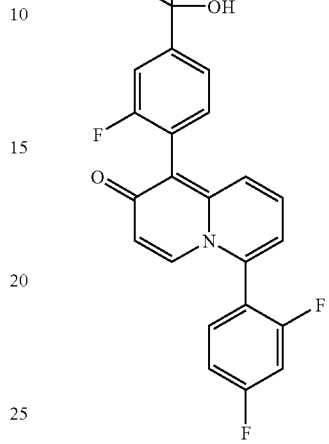

MS (ES): 410.2 (M+H).

EXAMPLE 54 methyl 6-(2,4-difluorophenyl)-1-(2,6-difluorophenyl)-2-oxo-2H-quinolizine-7-carboxylate

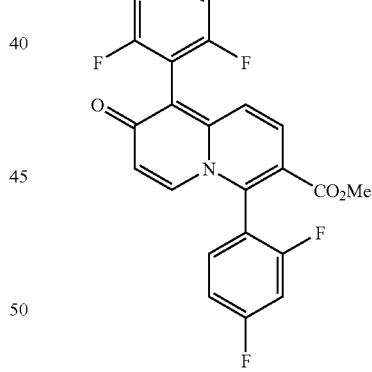

To a solution of 6-(2,4-difluorophenyl)-1-(2,6-difluorophenyl)-2-oxo-2H-quinolizine-7-carboxylic acid (Example 53, 21 mg) in THF/MeOH (1/1) was added EDC (20 mg) and HOBt (10 mg) at room temperature. After stirring for 2 h, the mixture was diluted with ethyl acetate and washed with water, brine, dried over MgSO$_4$ and concentrated. The residue was purified by silica gel (methylene chloride/methanol=20/1) to give the title compound (12 mg).

$^1$H NMR (CDCl$_3$) δ: 7.73 (d, 1H), 7.60 (d, 1H), 7.45 (m, 1H), 7.34 (m, 1H), 7.18 (m, 1H), 7.13 (m, 1H), 7.07 (m, 3H), 6.89 (d, 1H), 3.71 (s, 3H).
MS (ES): 428.2 (M+H).

EXAMPLE 55

6-(2,4-difluorophenyl)-1-(2,6-difluorophenyl)-2-oxo-2H-quinolizine-7-carboxamide

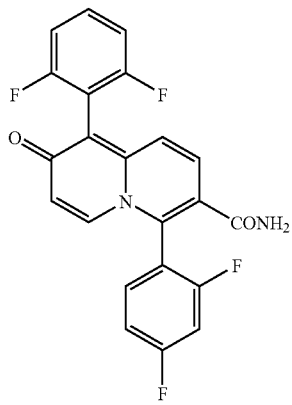

To a solution of 6-(2,4-difluorophenyl)-1-(2,6-difluorophenyl)-2-oxo-2H-quinolizine-7-carboxylic acid (Example 53, 21 mg) in THF was added EDC (20 mg), HOBt (10 mg) and ammonium hydroxide (0.1 mL) at room temperature. After stirring for 2 h, the mixture was diluted with ethyl acetate and washed with water, brine, dried over MgSO$_4$ and concentrated. The residue was purified by silica gel (methylene chloride/methanol=20/1) to give the title compound (17 mg).

$^1$H NMR (CDCl$_3$) δ: 7.71 (d, 1H), 7.54 (d, 1H), 7.45 (m, 1H), 7.37 (m, 1H), 7.17-7.03 (m, 5H), 6.88 (d, 1H).

MS (ES): 413.2 (M+H).

EXAMPLE 56

6-(2,4-difluorophenyl)-1-(2,6-difluorophenyl)-2-oxo-2H-quinolizine-7-carbaldehyde

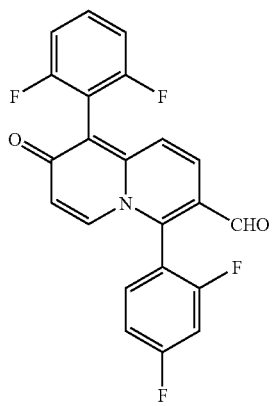

To a solution of 6-(2,4-difluorophenyl)-1-(2,6-difluorophenyl)-7-(hydroxymethyl)-2H-quinolizin-2-one (Example 52, 21 mg) was added Dess-Martin periodinane (30 mg) at room temperature and stirred for 12 h. The mixture was concentrated and purified by silica gel (methylene chloride/methanol=20/1) to give the title compound (8 mg).

$^1$H NMR (CDCl$_3$) δ: 9.40 (s, 1H), 7.71 (d, 1H), 7.58 (d, 1H), 7.54 (m, 1H), 7.45 (m, 1H), 7.30 (m, 1H), 7.24 (m, 1H), 7.08 (m, 3H), 6.89 (d, 1H).

MS (ES): 398.2 (M+H).

Examples 57-71 were made using procedures similar to that described in Example 37 to Example 48 above.

EXAMPLE 57 methyl 3-fluoro-4-[6-(4-fluorophenyl)-2-oxo-2H-quinolizin-1-yl]benzoate

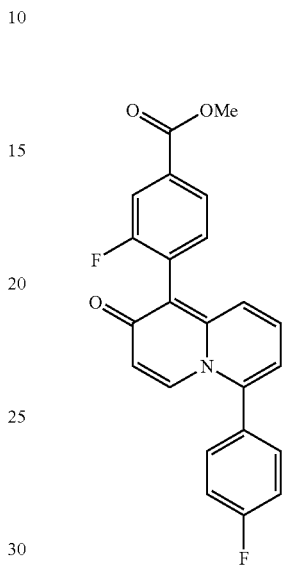

$^1$H NMR (CD$_3$OD) δ: 8.26 (d, 1H), 7.98 (d, 1H), 7.88 (d, 1H), 7.65 (m, 2H), 7.50 (t, 1H), 7.40 (m, 3H), 7.10 (d, 1H), 6.89 (m, 2H), 3.98 (s, 3H).

EXAMPLE 58

4-[6-(2,4-difluorophenyl)-2-oxo-2H-quinolizin-1-yl]-3-fluoro-N-methylbenzamide

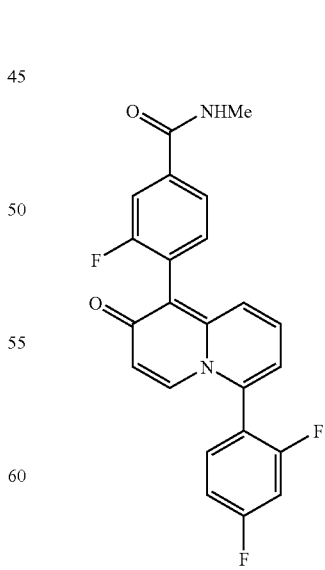

MS (ES): 409.1 (M+H).

EXAMPLE 61
4-[6-(2,4-difluorophenyl)-2-oxo-2H-quinolizin-1-yl]-3-fluoro-N-methoxy-N-methylbenzamide
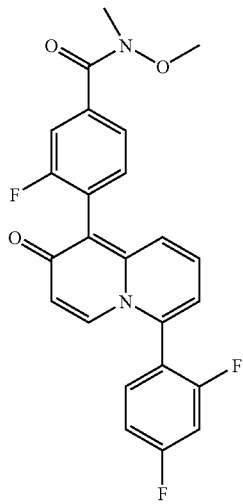
MS (ES): 439.2 (M+H).
EXAMPLE 62
methyl 4-[6-(2,4-difluorophenyl)-2-oxo-2H-quinolizin-1-yl]-3-fluorobenzoate
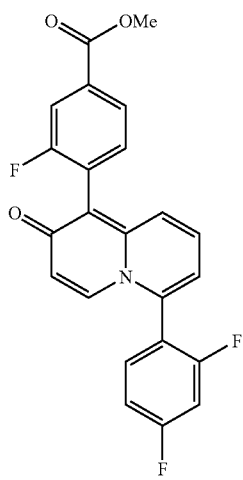
MS (ES): 410.2 (M+H).
EXAMPLE 63
6-(2,4-difluorophenyl)-1-[2-fluoro-4-(pyrrolidin-1-ylcarbonyl)phenyl]-2H-quinolizin-2-one
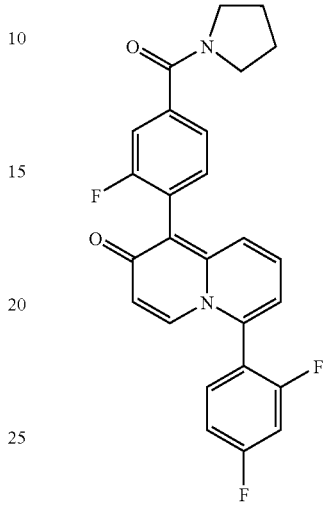
MS (ES): 449.2 (M+M).
EXAMPLE 64
1-[4-(azetidin-1-ylcarbonyl)-2-fluorophenyl]-6-(2,4-difluorophenyl)-2H-quinolizin-2-one
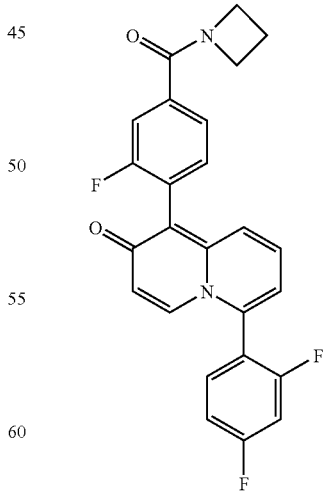
MS (ES): 435.1 (M+H).

EXAMPLE 65
1-(4-acetyl-2-fluorophenyl)-6-(2,4-difluorophenyl)-2H-quinolizin-2-one
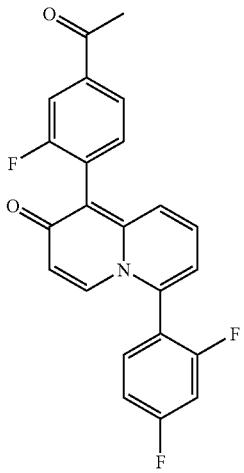
MS (ES): 394.1 (M+H).
EXAMPLE 66
1-(4-bromo-2,6-difluorophenyl)-6-(4-fluorophenyl)-2H-quinolizin-2-one
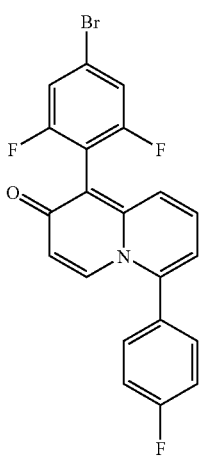
MS (ES): 432.0 (M+H).
EXAMPLE 67
1-(4-acetyl-2,6-difluorophenyl)-6-(4-fluorophenyl)-2H-quinolizin-2-one
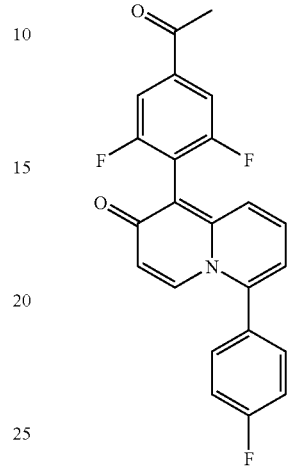
$^1$H NMR (CDCl$_3$, 500 MHz): δ 7.94 (d, 1H), 7.65 (d, 2H), 7.50 (m, 2H), 7.33 (t, 2H), 7.15 (dd, 1H), 6.94 (d, 1H), 6.80 (d, 1H), 6.55 (dd, 1H), 2.66 (s, 3H).
EXAMPLE 68
1-[2,6-difluoro-4-(1,3,4-oxadiazol-2-yl)phenyl]-6-(4-fluorophenyl)-2H-quinolizin-2-one
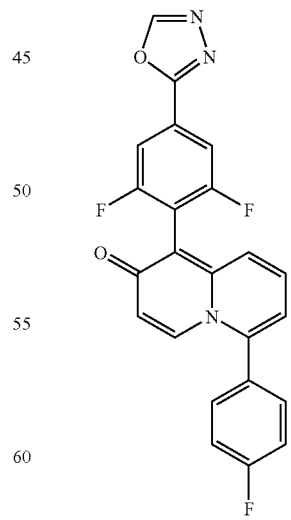
MS (ES): 420.1 (M+H).

EXAMPLE 69

3,5-difluoro-4-[6-(4-fluorophenyl)-2-oxo-2H-quinolizin-1-yl]benzonitrile

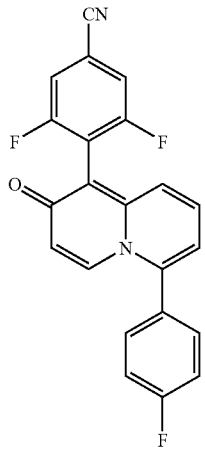

MS (ES): 377.3 (M+H).

EXAMPLE 70

3,5-difluoro-4-[6-(2-fluorophenyl)-2-oxo-2H-quinolizin-1-yl]benzonitrile

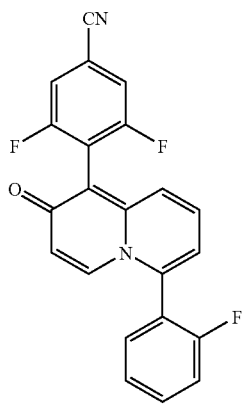

MS (ES): 377.2 (M+H).

EXAMPLE 71

6-(2,4-difluorophenyl)-1-[2-methoxy-5-(5-methyl-1,3,4-oxadiazol-2-yl)phenyl]-2H-quinolizin-2-one

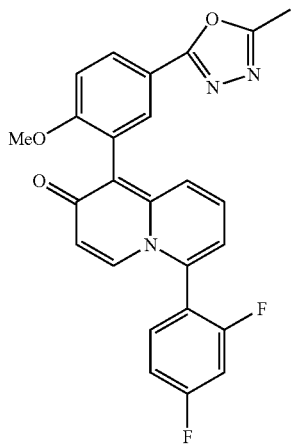

MS (ES): 446.2 (M+H).

EXAMPLE 72

6-(2,4-difluorophenyl)-1-[2-methoxy-5-(5-methyl-1,3,4-thiadiazol-2-yl)phenyl]-2H-quinolizin-2-one

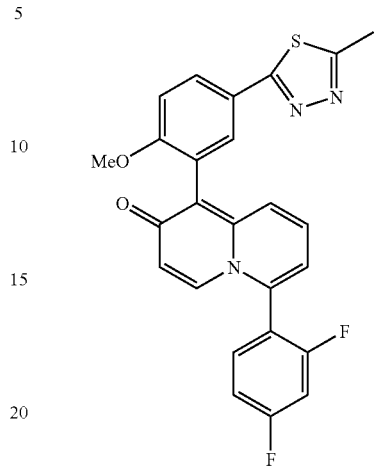

EXAMPLE 73

6-(2,4-difluorophenyl)-1-[2-fluoro-5-(5-methyl-1,3,4-thiadiazol-2-yl)phenyl]-2H-quinolizin-2-one

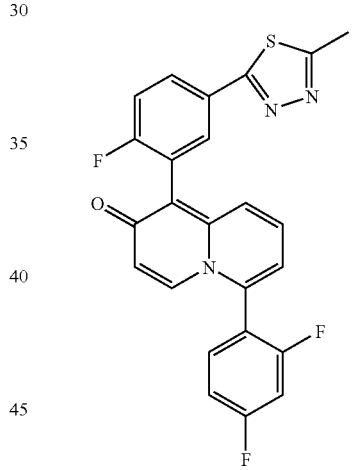

What is claimed is:

1. A compound represented by chemical formula (I) or a pharmaceutically acceptable salt thereof:

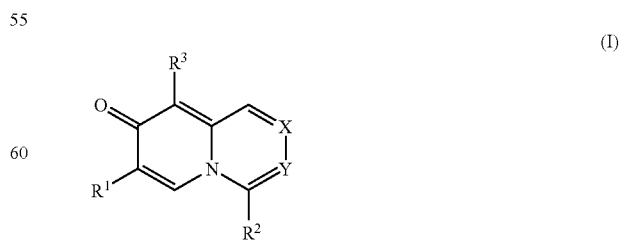

or a pharmaceutically acceptable salt thereof, wherein:
X and Y are each independently selected from —$CR^4$— and —N—;

$R^1$ is selected from:
 (1) hydrogen,
 (2) halogen,
 (3) OH, and
 (4) alkoxy;
$R^2$ is selected from:
 (1) $NR^a$,
 (2) aryl,
 (3) heteroaryl,
 (4) heterocycloalkyl, and
 (5) $OR^a$;
said heteroaryl, aryl and heterocycloalkyl are each optionally substituted with one or more substituents selected from $R^6$, $R^7$ and $R^8$;
$R^3$ is selected from:
 (1) aryl,
 (2) benzyl,
 (3) heteroaryl, and
 (4) heterocycloalkyl;
said heteroaryl, aryl and heterocycloalkyl are each optionally substituted with one or more substituents selected from $R^6$, $R^7$ and $R^8$;
$R^4$ is selected from:
 (1) hydrogen,
 (2) $C_1$-$C_6$ alkyl,
 (3) alkoxy,
 (4) CHO,
 (5) $CONH_2$,
 (6) $C(O)_2R^a$,
 (7) $C_0$-$C_4$alkyl-OH,
 (8) O—$C_1$-$C_4$ alkyl,
 (9) halogen,
 (10) aryl,
 (11) heteroaryl,
 (12) heterocycloalkyl,
 (13) $COR^a$,
 (14) O—C—C4alkyl-N—C(O)—$C_0$-$C_2$alkyl($R^bR^c$)—$NH_2$,
 (15) heterocycloalkyl-C(O)—$C_0$-$C_2$alkyl($R^bR^c$)—$NH_2$,
 (16) $N(R^a)(R^a)$,
 (17) O—$R^a$,
 (18) N—C(O)—N-heterocycloalkyl,
 (19) O—C(O)—N-heterocycloalkyl,
 (20) N—$C_1$-$C_4$alkyl-N—$R^a$, and
 (21) N—$C_1$-$C_4$alkyl-O—$R^a$;
said heteroaryl and aryl are each optionally substituted with one or more substituents selected from $R^6$, $R^7$ and $R^8$;
$R^6$, $R^7$ and $R^8$ are each independently selected from:
 (1) halogen,
 (2) $C_1$-$C_6$ alkyl,
 (3) CN,
 (4) $OR^a$,
 (5) alkoxy,
 (6) cycloalkyl,
 (7) C=$R^a(R^a)$,
 (8) $CON(R^a)(R^a)$,
 (9) aryl,
 (10) $N(R^a)(R^a)$,
 (11) heteroaryl,
 (12) hydrogen,
 (13) $C_1$-$C_4$—OH,
 (14) heterocycloalkyl,
 (15) CON-alkyl-$CO_2$—$R^a$,
 (16) CON-alkyl-$CON(R^a)(R^a)$,
 (17) CON-alkyl-$N(R^a)(R^a)$,
 (18) C(=O)$R^a$, and
 (19) $C(O)_2R^a$;

said heteroaryl and aryl are each optionally substituted with one or more substituents selected from $R^a$;
$R^a$ is selected from:
 (1) hydrogen,
 (2) halogen,
 (3) NH—$C_1$-$C_4$ alkyl,
 (4) $C_1$-$C_6$ alkyl,
 (5) $C_1$-$C_4$-alkyl-heteroaryl,
 (6) $C_1$-$C_4$-alkyl-cycloalkyl,
 (7) heteroaryl,
 (8) $C_1$-$C_4$alkyl-heterocycloalkyl,
 (9) heterocycloalkyl,
 (10) $C_0$-$C_4$alkyl-$NH_2$, and
 (11) $C_0$-$C_4$alkyl-OH;
$R^b$ and $R^c$ are each independently selected from hydrogen and alkyl, or $R^b$ and $R^c$ can join together to form a cycloalkyl.

2. A compound according to claim 1 represented by chemical Formula Ia, or a pharmaceutically acceptable salt thereof:

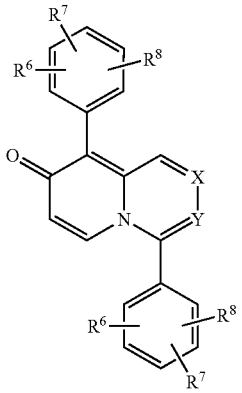

(Ia)

or a pharmaceutically acceptable salt thereof, wherein:
X and Y are each independently selected from —$CR^4$— and —N—;
$R^4$ is selected from:
 (1) hydrogen,
 (2) $C_1$-$C_6$ alkyl,
 (3) alkoxy,
 (4) CHO,
 (5) $CONH_2$,
 (6) $C(O)_2R^a$,
 (7) $C_0$-$C_4$alkyl-OH,
 (8) O—$C_1$-$C_4$ alkyl,
 (9) halogen,
 (10) aryl,
 (11) heteroaryl,
 (12) heterocycloalkyl,
 (13) $COR^a$,
 (14) O—$C_1$-$C_4$alkyl-N—C(O)—$C_0$-$C_2$alkyl($R^bR^c$)—$NH_2$,
 (15) heterocycloalkyl-C(O)—$C_0$-$C_2$alkyl($R^bR^c$)—$NH_2$,
 (16) $N(R^a)(R^a)$,
 (17) O—$R^a$,
 (18) N—C(O)—N-heterocycloalkyl,
 (19) O—C(O)—N-heterocycloalkyl,
 (20) N—$C_1$-$C_4$ alkyl-N—$R^a$, and
 (21) N—$C_1$-$C_4$alkyl-O—$R^a$;
said heteroaryl and aryl are each optionally substituted with one or more substituents selected from $R^6$, $R^7$ and $R^8$;
$R^6$, $R^7$ and $R^8$ are each independently selected from:
 (1) halogen,
 (2) $C_1$-$C_6$ alkyl,
 (3) CN, (4) $OR^a$,
(5) alkoxy.
(6) cycloalkyl,
(7) $C=R^a(R^a)$,
(8) $CON(R^a)(R^a)$,
(9) aryl,
(10) $N(R^a)(R^a)$,
(11) heteroaryl,
(12) hydrogen,
(13) $C_1$-$C_4$—OH,
(14) heterocycloalkyl,
(15) CON-alkyl-$CO_2$—$R^a$,
(16) CON-alkyl-$CON(R^a)(R^a)$,
(17) CON-alkyl-$N(R^a)(R^a)$,
(18) $C(=O)R^a$, and
(19) $C(O)_2R^a$;

said heteroaryl and aryl are each optionally substituted with one or more substituents selected from $R^a$; and
$R^a$ is selected from:
(1) hydrogen,
(2) halogen,
(3) NH—$C_1$-$C_4$ alkyl,
(4) $C_1$-$C_6$ alkyl,
(5) $C_1$-$C_4$-alkyl-heteroaryl,
(6) $C_1$-$C_4$-alkyl-cycloalkyl,
(7) heteroaryl,
(8) $C_1$-$C_4$alkyl-heterocycloalkyl,
(9) heterocycloalkyl,
(10) $C_0$-$C_4$alkyl-$NH_2$, and
(11) $C_0$-$C_4$alkyl-OH;

$R^b$ and $R^c$ are each independently selected from hydrogen and alkyl, or $R^b$ and $R^c$ can join together to form a cycloalkyl.

3. A compound according to claim 1 represented by the chemical Formula Ib, or a pharmaceutically acceptable salt thereof:

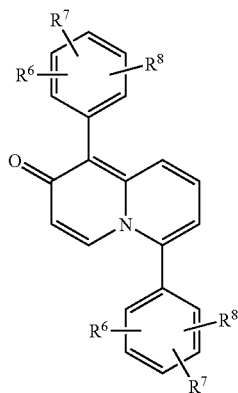

(Ib)

or a pharmaceutically acceptable salt thereof, wherein:
$R^6$, $R^7$ and $R^8$ are each independently selected from:
(1) halogen,
(2) $C_1$-$C_6$ alkyl,
(3) CN,
(4) $OR^a$,
(5) $CON(R^a)(R^a)$,
(6) aryl,
(7) heteroaryl,
(8) $C=R^a(R^a)$,
(9) hydrogen,
(10) $C_1$-$C_4$—OH,
(11) $C(=O)R^a$, and
(12) $C(O)_2R^a$;

said heteroaryl and aryl are each optionally substituted with one or more substituents selected from $R^a$; and
$R^a$ is selected from:
(1) hydrogen,
(2) halogen,
(3) NH—$C_1$-$C_4$ alkyl,
(4) $C_1$-$C_6$ alkyl,
(5) $C_1$-$C_4$-alkyl-heteroaryl,
(6) $C_1$-$C_4$-alkyl-cycloalkyl,
(7) heteroaryl,
(8) $C_1$-$C_4$alkyl-heterocycloalkyl,
(9) heterocycloalkyl,
(10) $C_0$-$C_4$alkyl-$NH_2$, and
(11) $C_0$-$C_4$alkyl-OH.

4. A compound represented by the chemical Formula Ic, or a pharmaceutically acceptable salt thereof:

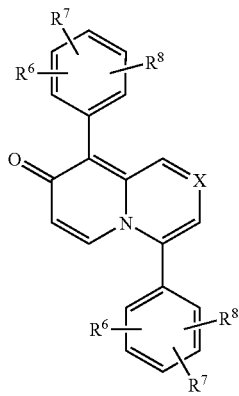

(Ic)

or a pharmaceutically acceptable salt thereof, wherein:
X is —$CR^4$—;
$R^4$ is selected from:
(1) hydrogen,
(2) $C_1$-$C_6$ alkyl,
(3) alkoxy,
(4) $CONH_2$,
(5) $C(O)_2R^a$,
(6) $C_0$-$C_4$alkyl-OH,
(7) O—$C_1$-$C_4$ alkyl,
(8) aryl,
(9) heteroaryl,
(10) heterocycloalkyl,
(11) $COR^a$,
(12) O—$C_1$-$C_4$alkyl-N—C(O)—$C_0$-$C_2$alkyl($R^bR^c$)—$NH_2$
(13) heterocycloalkyl-C(O)—$C_0$-$C_2$alkyl($R^bR^c$)—$NH_2$,
(14) $N(R^a)(R^a)$,
(15) O—$R^a$,
(16) N—C(O)—N-heterocycloalkyl,
(17) O—C(O)—N-heterocycloalkyl,
(18) N—$C_1$-$C_4$alkyl-N—$R^a$ and
(19) N—$C_1$-$C_4$alkyl-O—$R^a$;

said aryl and heteroaryl are each optionally substituted with one or more substituents selected from $R^6$, $R^7$ and $R^8$;
$R^6$, $R^7$ and $R^8$ are each independently selected from:
(1) halogen,
(2) $C_1$-$C_6$ alkyl,
(3) CN,
(4) $OR^a$,
(5) aryl,
(6) $C=R^a(R^a)$,
(7) heteroaryl, (8) hydrogen,
(9) $C_1$-$C_4$—OH, and
(10) C(=O)$R^a$;
said heteroaryl and aryl are each optionally substituted with one or more substituents selected from $R^a$;
$R^a$ is selected from:
(1) hydrogen,
(2) halogen,
(3) NH—$C_1$-$C_4$ alkyl,
(4) $C_1$-$C_6$ alkyl,
(5) $C_1$-$C_4$-alkyl-heteroaryl,
(6) $C_1$-$C_4$-alkyl-cycloalkyl,
(7) heteroaryl,
(8) $C_1$-$C_4$alkyl-heterocycloalkyl,
(9) heterocycloalkyl,
(10) $C_0$-$C_4$alkyl-$NH_2$, and
(11) $C_0$-$C_4$alkyl-OH;
$R^b$ and $R^c$ are each independently selected from hydrogen and alkyl, or $R^b$ and $R^c$ can join together to form a cycloalkyl.

5. A compound represented by the chemical Formula Id, or a pharmaceutically acceptable salt thereof:

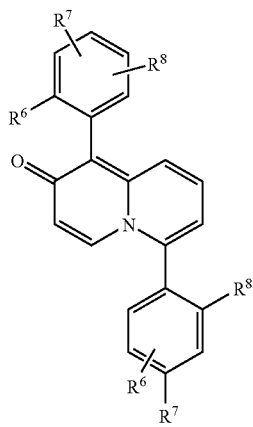

(Id)

or a pharmaceutically acceptable salt thereof, wherein:
$R^6$, $R^7$ and $R^8$ are each independently selected from:
(1) halogen,
(2) $C_1$-$C_6$ alkyl,
(3) CN,
(4) $OR^a$,
(5) CON($R^a$)($R^a$),
(6) aryl,
(7) heteroaryl,
(8) hydrogen,
(9) $C_1$-$C_4$—OH,
(10) C(=O)$R^a$, and
(11) C(O)$_2R^a$;
said heteroaryl and aryl are each optionally substituted with one or more substituents selected from $R^a$;
$R^a$ is selected from:
(1) hydrogen,
(2) halogen,
(3) NH—$C_1$-$C_4$ alkyl,
(4) $C_1$-$C_6$ alkyl,
(5) $C_1$-$C_4$-alkyl-heteroaryl,
(6) $C_1$-$C_4$-alkyl-cycloalkyl,
(7) heteroaryl,
(8) $C_1$-$C_4$alkyl-heterocycloalkyl,
(9) heterocycloalkyl,
(10) $C_0$-$C_4$alkyl-$NH_2$, and
(11) $C_0$-$C_4$alkyl-OH.

6. The compound according to claim 1, represented by

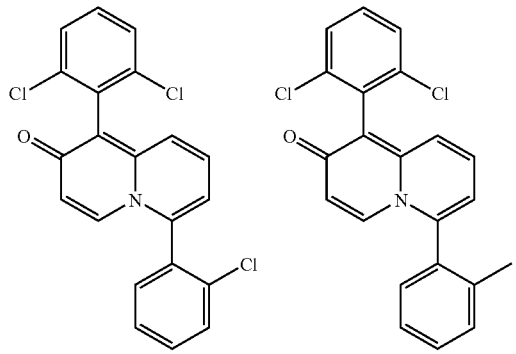

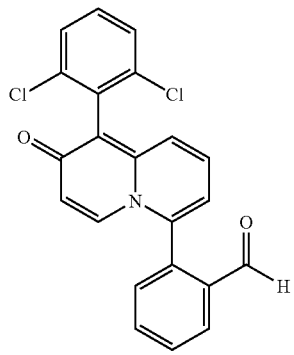

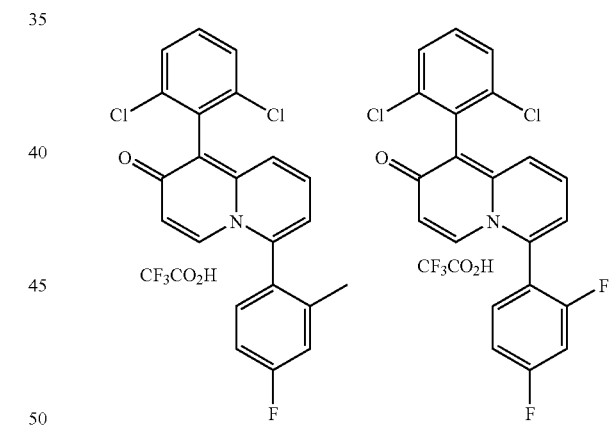

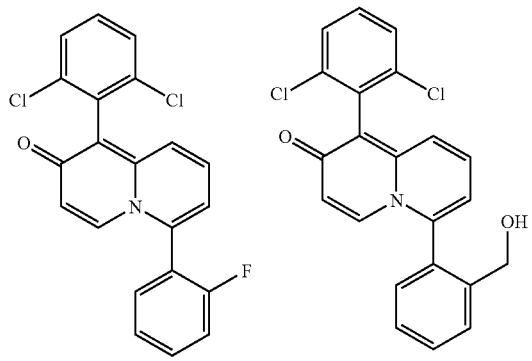

-continued
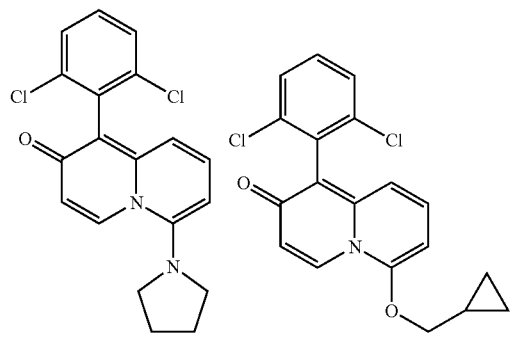 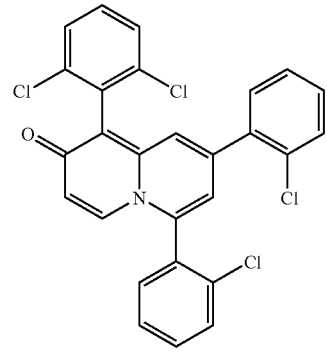
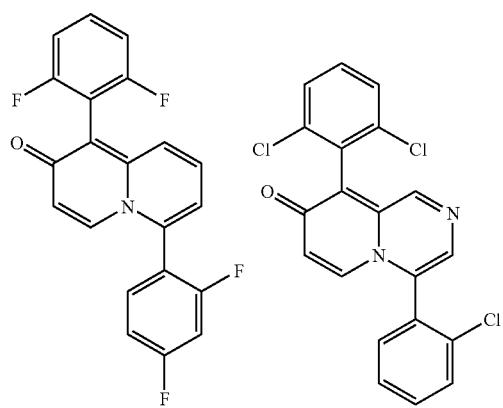 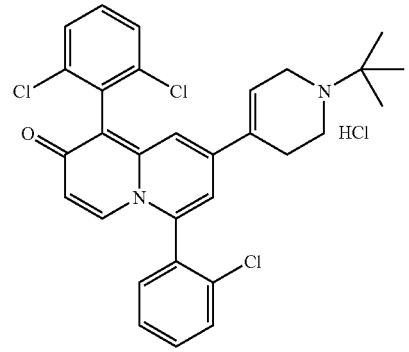
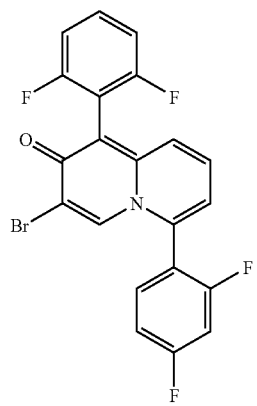 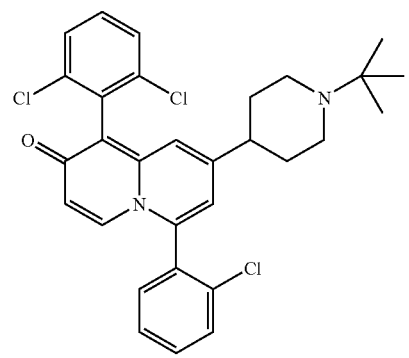
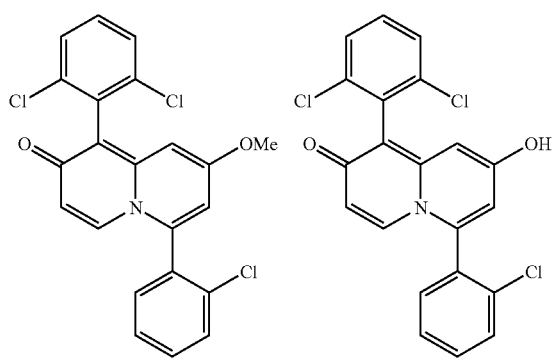 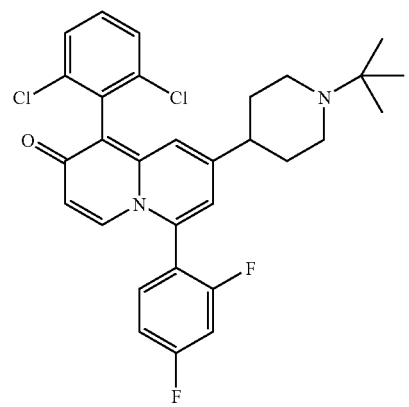

-continued
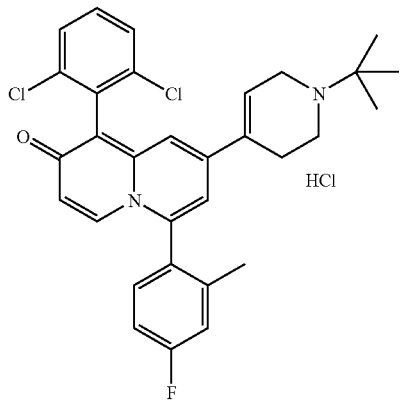
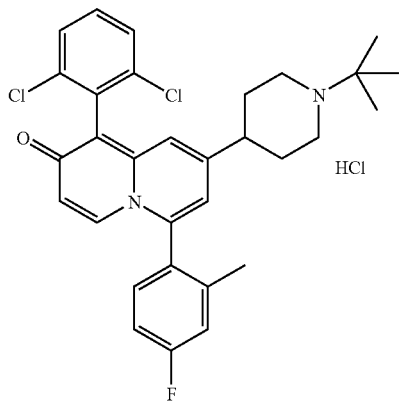
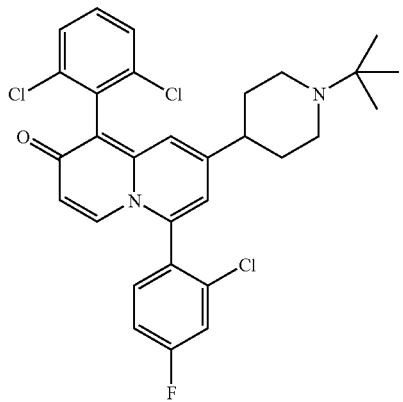
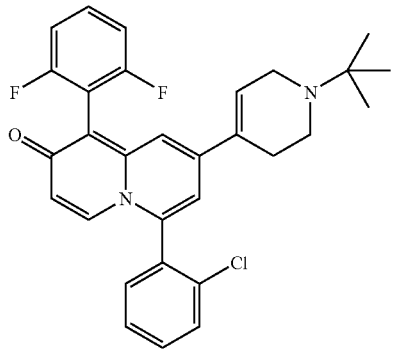
-continued
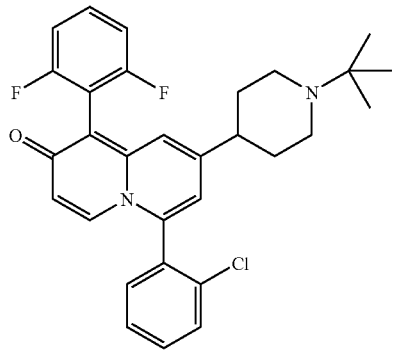
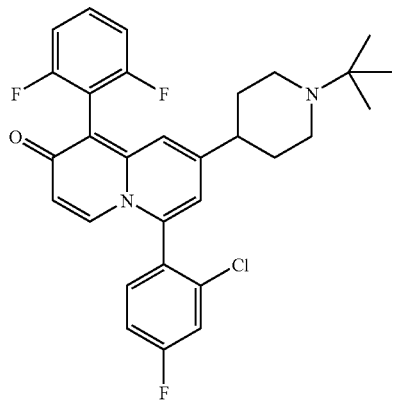
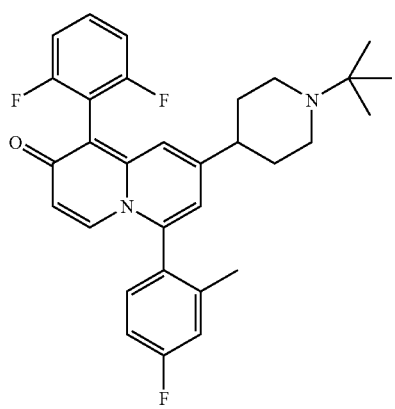
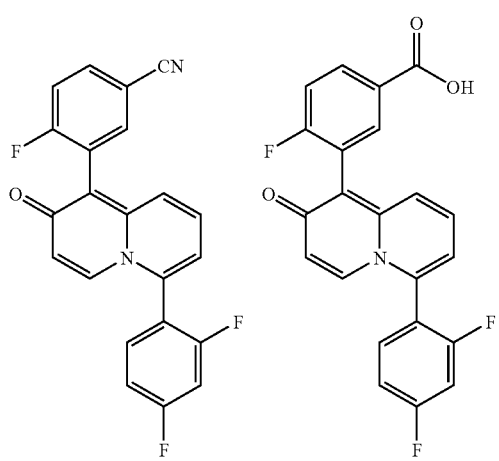

-continued
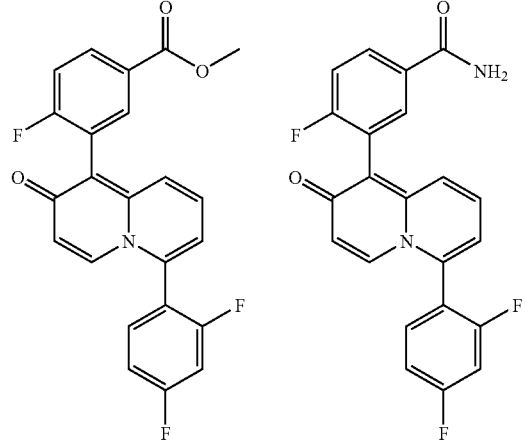
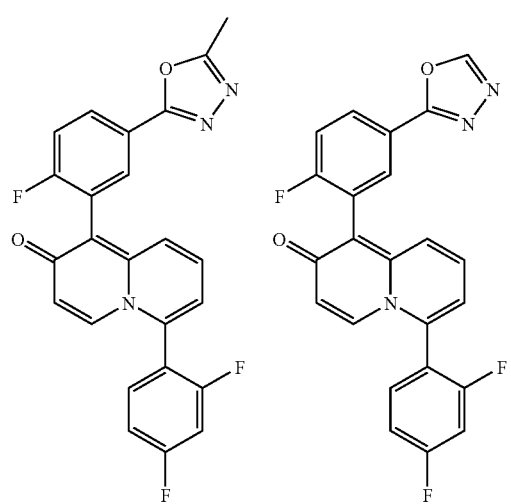
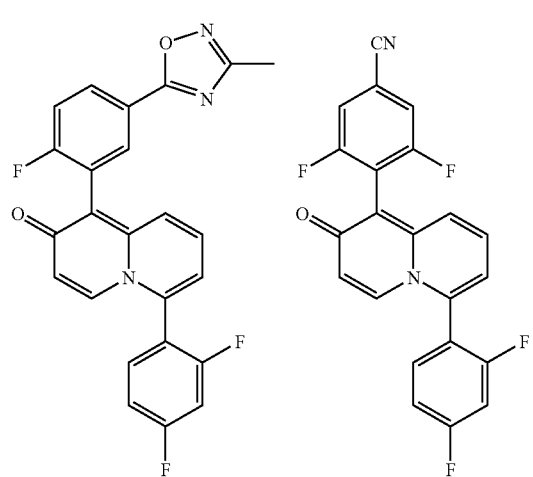
-continued
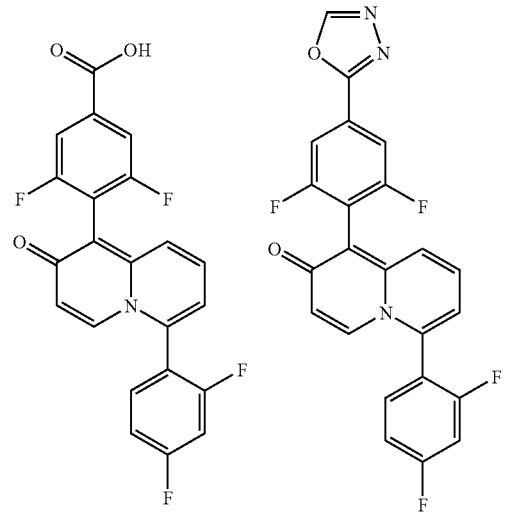
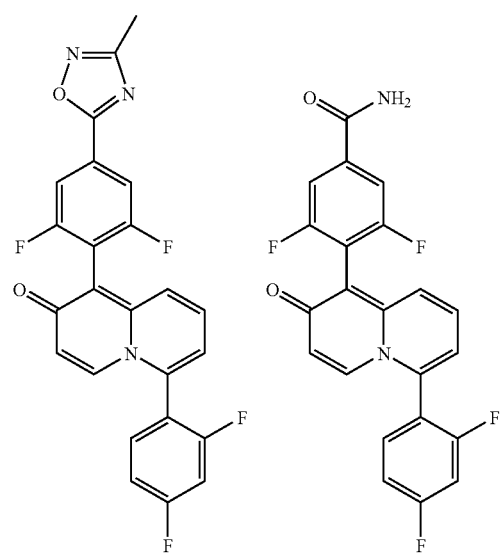

-continued
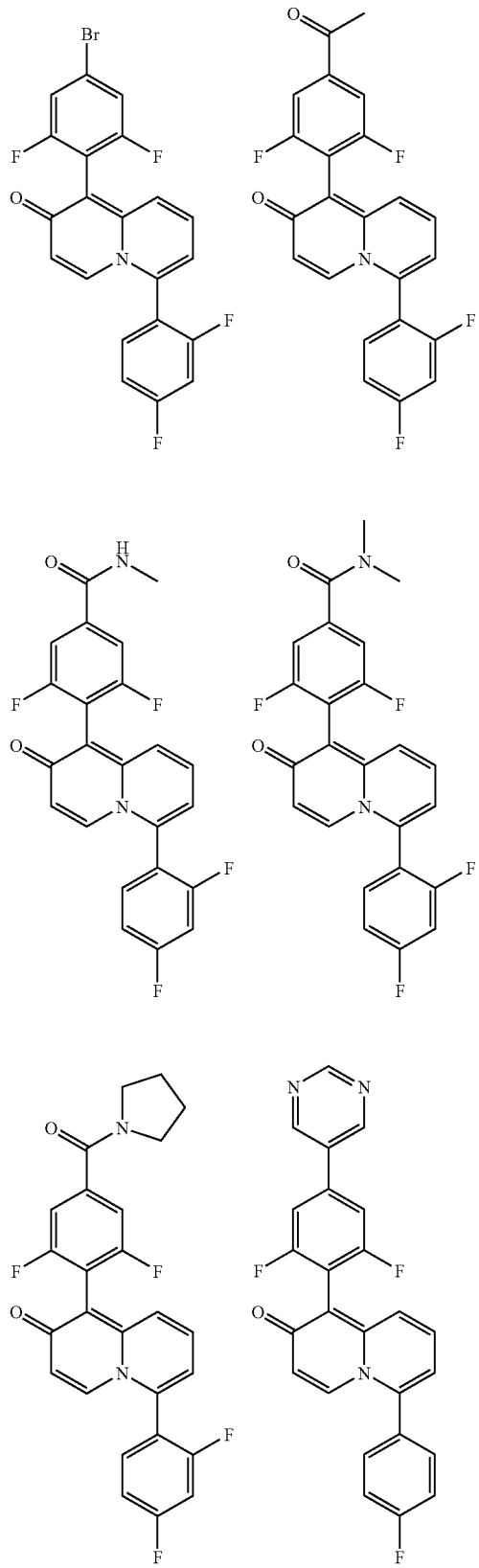
-continued
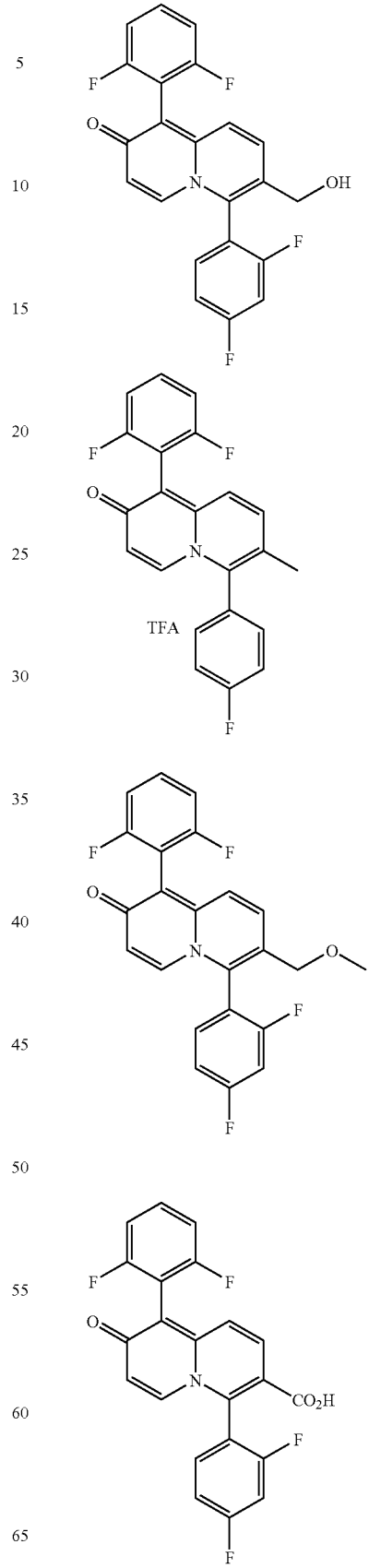

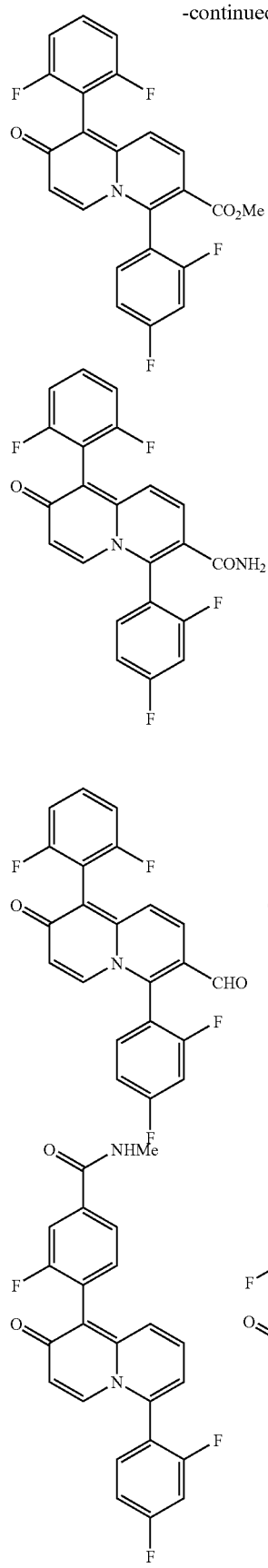
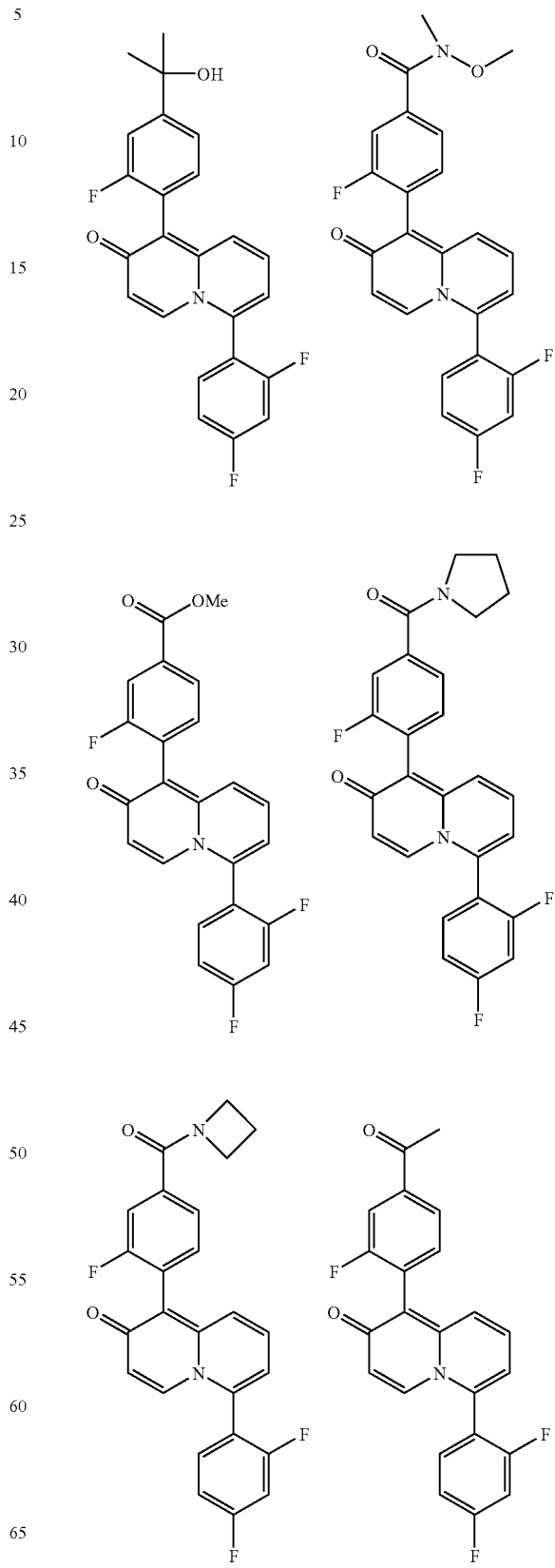

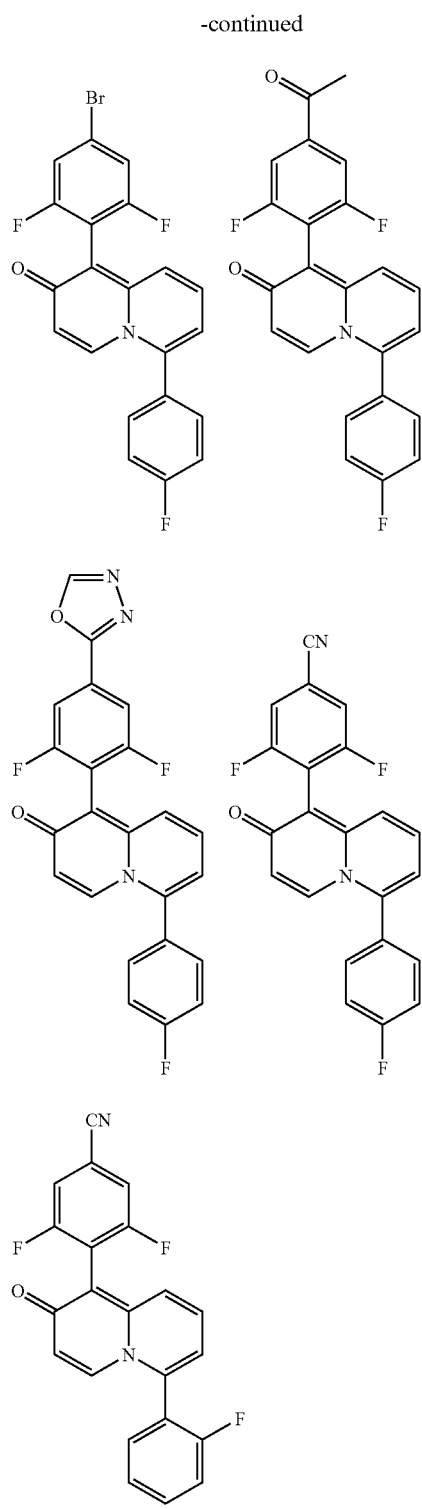
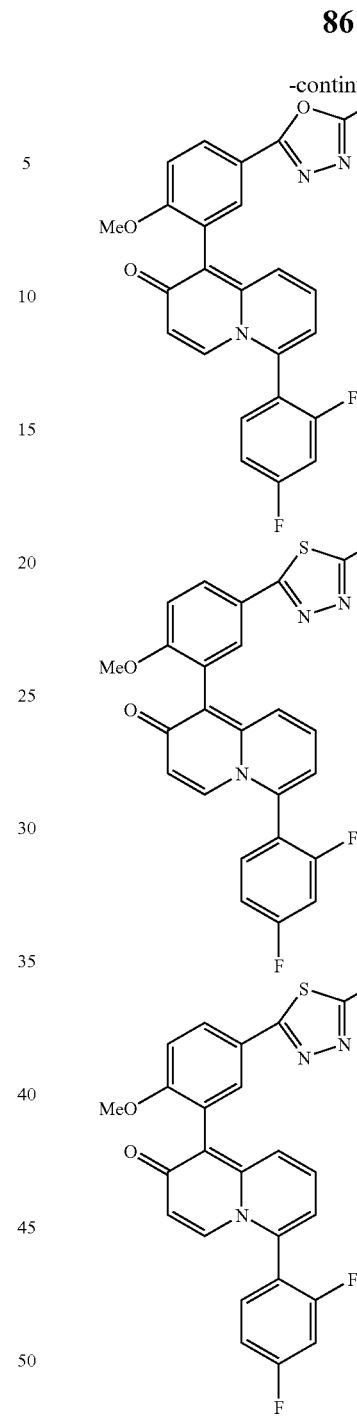
or a pharmaceutically acceptable salt thereof.
7. A pharmaceutical composition comprising an inert carrier and an effective amount of a compound according to claim 1.
* * * * *